(12) United States Patent
Shuros et al.

(10) Patent No.: US 9,415,225 B2
(45) Date of Patent: *Aug. 16, 2016

(54) METHOD AND APPARATUS FOR PACING DURING REVASCULARIZATION

(71) Applicant: Cardiac Pacemakers, Inc., St. Paul, MN (US)

(72) Inventors: Allan C. Shuros, St. Paul, MN (US); Tamara Colette Baynham, Piscataway, NJ (US); Jihong Qu, Maple Grove, MN (US); Joseph M. Pastore, Concord, OH (US); Andrew P. Kramer, Marine on St. Croix, MN (US); Frits W. Prinzen, Maastricht (NL); Ward Y. R. Vanagt, Maastricht (NL); Richard N. Cornelussen, Maastricht (NL)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,599

(22) Filed: Mar. 15, 2013

(65) Prior Publication Data

US 2013/0268014 A1    Oct. 10, 2013

Related U.S. Application Data

(63) Continuation of application No. 13/113,706, filed on May 23, 2011, now Pat. No. 8,452,400, which is a continuation of application No. 11/113,828, filed on Apr. 25, 2005, now Pat. No. 7,962,208.

(51) Int. Cl.
*A61N 1/08* (2006.01)
*A61N 1/362* (2006.01)
(Continued)

(52) U.S. Cl.
CPC ............... *A61N 1/362* (2013.01); *A61B 17/22* (2013.01); *A61B 18/1492* (2013.01);
(Continued)

(58) Field of Classification Search
CPC .......................... A61N 1/3625; A61N 1/056
USPC ............................... 607/2, 3, 9, 119
See application file for complete search history.

(56) References Cited

U.S. PATENT DOCUMENTS 15,192 A    6/1856    Peale
2,682,057 A    6/1954    Lord
(Continued)

FOREIGN PATENT DOCUMENTS

CA    2459408 A1    3/2003
DE    3300050    7/1984
(Continued)

OTHER PUBLICATIONS

"U.S. Appl. No. 11/030,575, Non Final Office Action mailed Jul. 26, 2006", 10 pgs.
(Continued)

*Primary Examiner* — Joseph Dietrich
(74) *Attorney, Agent, or Firm* — Schwegman Lundberg & Woessner, P.A.

(57) ABSTRACT

A system for use during revascularization includes a catheter having an adjustable balloon for delivery a stent, one or more pacing electrodes for delivering one or more pacing pulses to a patient's heart, and a pacemaker configured to generate the one or more pacing pulses to be delivered to the heart via the one or more pacing electrodes. The one or more pacing pulses are delivered at a rate substantially higher than the patient's intrinsic heart rate without being synchronized to the patient's intrinsic cardiac contractions, and are delivered before, during, or after an ischemic event to prevent or reduce cardiac injury.

20 Claims, 6 Drawing Sheets

(51) Int. Cl.
*A61B 18/14* (2006.01)
*A61N 1/05* (2006.01)
*A61N 5/10* (2006.01)
*A61B 17/22* (2006.01)
*A61B 18/00* (2006.01)

(52) U.S. Cl.
CPC .............. *A61N 1/056* (2013.01); *A61N 1/3625* (2013.01); *A61N 5/1001* (2013.01); *A61B 2017/22001* (2013.01); *A61B 2018/0041* (2013.01); *A61B 2018/00214* (2013.01); *A61B 2018/00422* (2013.01); *A61N 2001/0585* (2013.01)

(56) References Cited

U.S. PATENT DOCUMENTS

| | | |
|---|---|---|
| 2,701,559 A | 2/1955 | Cooper |
| 2,832,076 A | 4/1958 | Polachek et al. |
| 3,099,016 A | 7/1963 | Edwards |
| 3,111,358 A | 11/1963 | Doerr |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,769,984 A | 11/1973 | Muench |
| 3,795,246 A | 3/1974 | Sturgeon |
| 3,837,347 A | 9/1974 | Tower |
| 3,839,741 A | 10/1974 | Haller |
| 3,865,118 A | 2/1975 | Bures |
| 3,868,956 A | 3/1975 | Alfidi et al. |
| 3,874,388 A | 4/1975 | King et al. |
| 3,893,461 A | 7/1975 | Preston |
| 3,915,174 A | 10/1975 | Preston |
| 3,942,536 A | 3/1976 | Mirowski et al. |
| 3,949,757 A | 4/1976 | Sabel |
| 3,997,923 A | 12/1976 | Possis |
| 4,030,508 A | 6/1977 | Thalen |
| 4,035,849 A | 7/1977 | Angell et al. |
| 4,056,854 A | 11/1977 | Boretos et al. |
| 4,094,321 A | 6/1978 | Muto |
| 4,106,129 A | 8/1978 | Carpentier et al. |
| 4,124,031 A | 11/1978 | Mensink et al. |
| 4,136,702 A | 1/1979 | Trabucco |
| 4,202,339 A | 5/1980 | Wirtzfeld et al. |
| 4,222,126 A | 9/1980 | Boretos et al. |
| 4,233,690 A | 11/1980 | Akins |
| 4,262,982 A | 4/1981 | Kenny |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,365,639 A | 12/1982 | Goldreyer |
| 4,373,216 A | 2/1983 | Klawitter |
| 4,388,930 A | 6/1983 | De Bellis |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,587,975 A | 5/1986 | Salo et al. |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,702,253 A | 10/1987 | Nappholz et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,763,655 A | 8/1988 | Wirtzfeld et al. |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,809,697 A | 3/1989 | Causey, III et al. |
| 4,811,975 A | 3/1989 | Paul, Jr. et al. |
| 4,829,990 A | 5/1989 | Thuroff et al. |
| 4,834,710 A | 5/1989 | Fleck |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,882,777 A | 11/1989 | Narula |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,919,133 A | 4/1990 | Chiang |
| 4,922,905 A | 5/1990 | Strecker |
| 4,927,426 A | 5/1990 | Dretler |
| 4,954,126 A | 9/1990 | Wallsten |
| 4,955,382 A | 9/1990 | Franz et al. |
| 4,962,767 A | 10/1990 | Brownlee |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,427 A | 4/1991 | Suzuki et al. |
| 5,007,896 A | 4/1991 | Shiber |
| 5,025,786 A | 6/1991 | Siegel |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,072,458 A | 12/1991 | Suzuki |
| 5,080,668 A | 1/1992 | Bolz et al. |
| 5,085,635 A | 2/1992 | Cragg |
| 5,089,015 A | 2/1992 | Ross |
| 5,099,839 A | 3/1992 | Miyata et al. |
| 5,111,818 A | 5/1992 | Suzuki et al. |
| 5,121,750 A | 6/1992 | Katims |

(56) References Cited

U.S. PATENT DOCUMENTS

| | | |
|---|---|---|
| 5,127,403 A | 7/1992 | Brownlee |
| 5,131,406 A | 7/1992 | Kaltenbach |
| 5,132,473 A | 7/1992 | Furutaka et al. |
| 5,141,494 A | 8/1992 | Danforth et al. |
| 5,143,089 A | 9/1992 | Alt |
| 5,152,771 A | 10/1992 | Sabbaghian et al. |
| 5,154,169 A | 10/1992 | Miyata et al. |
| 5,154,387 A | 10/1992 | Trailer |
| 5,156,157 A | 10/1992 | Valenta, Jr. et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,170,802 A | 12/1992 | Mehra |
| 5,209,741 A | 5/1993 | Spaeth |
| 5,215,541 A | 6/1993 | Nashef |
| 5,217,483 A | 6/1993 | Tower |
| 5,258,023 A | 11/1993 | Reger |
| 5,258,042 A | 11/1993 | Mehta |
| 5,261,419 A | 11/1993 | Osypka |
| 5,282,847 A | 2/1994 | Trescony et al. |
| 5,285,781 A | 2/1994 | Brodard |
| 5,295,958 A | 3/1994 | Shturman |
| 5,314,460 A | 5/1994 | Borghi |
| 5,332,402 A | 7/1994 | Teitelbaum |
| 5,334,221 A | 8/1994 | Bardy |
| 5,336,251 A | 8/1994 | Borghi |
| 5,336,258 A | 8/1994 | Quintero et al. |
| 5,350,398 A | 9/1994 | Pavcnik et al. |
| 5,356,427 A | 10/1994 | Miyata et al. |
| 5,360,444 A | 11/1994 | Kusuhara |
| 5,370,685 A | 12/1994 | Stevens |
| 5,374,287 A | 12/1994 | Rubin |
| 5,387,232 A | 2/1995 | Trailer |
| 5,389,106 A | 2/1995 | Tower |
| 5,397,351 A | 3/1995 | Pavcnik et al. |
| 5,409,019 A | 4/1995 | Wilk |
| 5,411,535 A | 5/1995 | Fujii et al. |
| 5,411,552 A | 5/1995 | Andersen et al. |
| 5,423,806 A | 6/1995 | Dale et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,466,255 A | 11/1995 | Franchi |
| 5,476,502 A | 12/1995 | Rubin |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,483,022 A | 1/1996 | Mar |
| 5,484,419 A | 1/1996 | Fleck |
| 5,496,354 A | 3/1996 | DeBellis |
| 5,500,014 A | 3/1996 | Quijano et al. |
| 5,507,767 A | 4/1996 | Maeda et al. |
| 5,507,787 A | 4/1996 | Borghi |
| 5,531,779 A | 7/1996 | Dahl et al. |
| 5,534,007 A | 7/1996 | St. Germain et al. |
| 5,545,133 A | 8/1996 | Burns et al. |
| 5,545,191 A | 8/1996 | Mann et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,159 A | 11/1996 | Alt |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,588,432 A | 12/1996 | Crowley |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,634,899 A | 6/1997 | Shapland et al. |
| 5,645,559 A | 7/1997 | Hachtman et al. |
| 5,662,671 A | 9/1997 | Barbut et al. |
| 5,667,523 A | 9/1997 | Bynon |
| 5,674,217 A | 10/1997 | Wahlstrom et al. |
| 5,674,277 A | 10/1997 | Freitag |
| 5,693,083 A | 12/1997 | Baker |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,761 A | 5/1998 | Obino |
| 5,755,764 A | 5/1998 | Schroeppel |
| 5,756,476 A | 5/1998 | Epstein et al. |
| 5,760,341 A | 6/1998 | Laske et al. |
| 5,769,812 A | 6/1998 | Stevens et al. |
| 5,772,693 A | 6/1998 | Brownlee |
| 5,797,903 A | 8/1998 | Swanson et al. |
| 5,800,456 A | 9/1998 | Maeda et al. |
| 5,800,496 A | 9/1998 | Swoyer et al. |
| 5,800,531 A | 9/1998 | Cosgrove et al. |
| 5,807,405 A | 9/1998 | Vanney |
| 5,814,076 A | 9/1998 | Brownlee |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,132 A | 12/1998 | Ilvento |
| 5,843,158 A | 12/1998 | Lenker et al. |
| 5,851,206 A | 12/1998 | Guglielmi et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,207 A | 5/1999 | Shen |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,921,935 A | 7/1999 | Hickey |
| 5,925,063 A | 7/1999 | Khosravi |
| 5,935,160 A | 8/1999 | Auricchio et al. |
| 5,944,738 A | 8/1999 | Amplatz |
| 5,954,761 A | 9/1999 | Machek et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,536 A | 12/1999 | Osswald et al. |
| 5,997,557 A | 12/1999 | Barbut et al. |
| 6,010,522 A | 1/2000 | Barbut et al. |
| 6,014,579 A | 1/2000 | Pomeranz et al. |

(56) References Cited

U.S. PATENT DOCUMENTS

| | | |
|---|---|---|
| 6,022,370 A | 2/2000 | Tower |
| 6,023,638 A | 2/2000 | Swanson |
| 6,027,520 A | 2/2000 | Tsugita et al. |
| 6,027,525 A | 2/2000 | Suh et al. |
| 6,042,598 A | 3/2000 | Tsugita |
| 6,042,607 A | 3/2000 | Williamson, IV et al. |
| 6,051,014 A | 4/2000 | Jang |
| 6,056,742 A | 5/2000 | Murphy-Chutorian et al. |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya |
| 6,132,390 A | 10/2000 | Cookston et al. |
| 6,132,473 A | 10/2000 | Williams |
| 6,142,987 A | 11/2000 | Tsugita |
| 6,146,366 A | 11/2000 | Schachar |
| 6,156,061 A | 12/2000 | Wallace et al. |
| 6,161,029 A | 12/2000 | Spreigl et al. |
| 6,162,245 A | 12/2000 | Jayaraman |
| 6,165,200 A | 12/2000 | Tsugita et al. |
| 6,165,209 A | 12/2000 | Patterson et al. |
| 6,167,315 A | 12/2000 | Coe et al. |
| 6,168,579 B1 | 1/2001 | Tsugita |
| 6,168,614 B1 | 1/2001 | Andersen |
| 6,171,327 B1 | 1/2001 | Daniel et al. |
| 6,171,335 B1 | 1/2001 | Wheatley et al. |
| 6,178,354 B1 | 1/2001 | Gibson |
| 6,179,859 B1 | 1/2001 | Bates et al. |
| 6,183,469 B1 | 2/2001 | Thapliyal et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,238,390 B1 | 5/2001 | Tu et al. |
| 6,241,727 B1 | 6/2001 | Tu et al. |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Letendre et al. |
| 6,270,513 B1 | 8/2001 | Tsugita et al. |
| 6,272,379 B1 | 8/2001 | Fischell et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel et al. |
| 6,324,434 B2 | 11/2001 | Coe et al. |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,366,808 B1 | 4/2002 | Schroeppel et al. |
| 6,371,970 B1 | 4/2002 | Khosravi et al. |
| 6,371,983 B1 | 4/2002 | Lane |
| 6,379,351 B1 | 4/2002 | Thapliyal et al. |
| 6,379,383 B1 | 4/2002 | Palmaz et al. |
| 6,397,109 B1 | 5/2002 | Cammilli et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | Dimatteo et al. |
| 6,449,507 B1 | 9/2002 | Hill et al. |
| 6,451,016 B1 | 9/2002 | Karakozian |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,477,402 B1 | 11/2002 | Lynch et al. |
| 6,477,427 B1 | 11/2002 | Stolz et al. |
| 6,482,228 B1 | 11/2002 | Norred |
| 6,485,501 B1 | 11/2002 | Green et al. |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,501,983 B1 | 12/2002 | Natarajan et al. |
| 6,503,272 B2 | 1/2003 | Duerig et al. |
| 6,508,833 B2 | 1/2003 | Pavcnik et al. |
| 6,512,957 B1 | 1/2003 | Witte |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,532,388 B1 | 3/2003 | Hill et al. |
| 6,537,297 B2 | 3/2003 | Tsugita et al. |
| 6,540,765 B1 | 4/2003 | Malacoff |
| 6,540,768 B1 | 4/2003 | Diaz et al. |
| 6,542,774 B2 | 4/2003 | Hill et al. |
| 6,562,058 B2 | 5/2003 | Seguin et al. |
| 6,569,145 B1 | 5/2003 | Shmulewitz et al. |
| 6,569,196 B1 | 5/2003 | Vesely |
| 6,572,643 B1 | 6/2003 | Gharibadeh |
| 6,584,362 B1 | 6/2003 | Scheiner et al. |
| 6,592,546 B1 | 7/2003 | Barbut et al. |
| 6,592,614 B2 | 7/2003 | Lenker |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,628,987 B1 | 9/2003 | Hill et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,638,278 B2 | 10/2003 | Falwell et al. |
| 6,640,120 B1 | 10/2003 | Swanson et al. |
| 6,652,571 B1 | 11/2003 | White et al. |
| 6,652,578 B2 | 11/2003 | Bailey et al. |
| 6,663,588 B2 | 12/2003 | BuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,690,970 B1 | 2/2004 | Taheri et al. |
| 6,692,512 B2 | 2/2004 | Jang |
| 6,695,864 B2 | 2/2004 | Macoviak et al. |
| 6,695,865 B2 | 2/2004 | Boyle et al. |
| 6,697,676 B2 | 2/2004 | Dahl |
| 6,702,851 B1 | 3/2004 | Chinn et al. |
| 6,709,390 B1 | 3/2004 | Marie Pop |
| 6,711,436 B1 | 3/2004 | Duhaylongsod |
| 6,711,440 B2 | 3/2004 | Deal et al. |
| 6,712,842 B1 | 3/2004 | Gifford, III et al. |
| 6,712,843 B2 | 3/2004 | Elliott |
| 6,714,842 B1 | 3/2004 | Ito |
| 6,718,208 B2 | 4/2004 | Hill et al. |

(56) References Cited

U.S. PATENT DOCUMENTS

| | | |
|---|---|---|
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,735,471 B2 | 5/2004 | Hill et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,772,014 B2 | 8/2004 | Coe et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| RE38,654 E | 11/2004 | Hill et al. |
| 6,813,516 B2 | 11/2004 | Ujhelyi et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| RE38,705 E | 2/2005 | Hill et al. |
| 6,849,085 B2 | 2/2005 | Marton |
| 6,863,668 B2 | 3/2005 | Gillespie et al. |
| 6,865,420 B1 | 3/2005 | Kroll |
| 6,866,650 B2 | 3/2005 | Stevens et al. |
| 6,866,669 B2 | 3/2005 | Buzzard |
| 6,872,223 B2 | 3/2005 | Roberts et al. |
| 6,872,226 B2 | 3/2005 | Cali |
| 6,875,231 B2 | 4/2005 | Anduiza |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,904,318 B2 | 6/2005 | Hill et al. |
| 6,905,743 B1 | 6/2005 | Chen et al. |
| 6,908,481 B2 | 6/2005 | Cribier |
| 6,909,920 B2 | 6/2005 | Lokhoff et al. |
| 6,911,036 B2 | 6/2005 | Douk et al. |
| 6,911,043 B2 | 6/2005 | Myers et al. |
| 6,912,419 B2 | 6/2005 | Hill et al. |
| 6,936,058 B2 | 8/2005 | Forde et al. |
| 6,936,067 B2 | 8/2005 | Buchanan |
| 6,939,352 B2 | 9/2005 | Buzzard |
| 6,950,701 B2 | 9/2005 | Begemann et al. |
| 6,951,571 B1 | 10/2005 | Srivastava |
| 6,953,332 B1 | 10/2005 | Kurk |
| 6,964,673 B2 | 11/2005 | Tsugita et al. |
| 6,969,395 B2 | 11/2005 | Eskuri |
| 6,972,025 B2 | 12/2005 | WasDyke et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,980,858 B2 | 12/2005 | Fuimaono et al. |
| 6,984,242 B2 | 1/2006 | Campbell |
| 6,988,001 B2 | 1/2006 | Greatbatch et al. |
| 6,989,027 B2 | 1/2006 | Allen |
| 6,994,314 B2 | 2/2006 | Garnier et al. |
| 6,999,809 B2 | 2/2006 | Currier et al. |
| 6,999,821 B2 | 2/2006 | Jenney et al. |
| 7,003,350 B2 | 2/2006 | Denker et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,029,467 B2 | 4/2006 | Currier et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,115,141 B2 | 10/2006 | Menz et al. |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,184,829 B2 | 2/2007 | Hill et al. |
| 7,189,258 B2 | 3/2007 | Johnson et al. |
| 7,191,018 B2 | 3/2007 | Gielen et al. |
| 7,201,772 B2 | 4/2007 | Schwammenthal |
| 7,225,019 B2 | 5/2007 | Jahns et al. |
| 7,235,093 B2 | 6/2007 | Gregorich |
| 7,236,821 B2 | 6/2007 | Cates et al. |
| 7,258,696 B2 | 8/2007 | Rabkin et al. |
| 7,267,686 B2 | 9/2007 | DiMatteo et al. |
| 7,269,457 B2 | 9/2007 | Shafer et al. |
| 7,276,078 B2 | 10/2007 | Spenser et al. |
| 7,295,874 B2 | 11/2007 | Prinzen et al. |
| 7,322,932 B2 | 1/2008 | Xie et al. |
| 7,326,236 B2 | 2/2008 | Andreas et al. |
| 7,329,279 B2 | 2/2008 | Haug |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,422,585 B1 | 9/2008 | Eggers et al. |
| 7,445,631 B2 | 11/2008 | Salahieh et al. |
| 7,470,285 B2 | 12/2008 | Nugent |
| 7,473,417 B2 | 1/2009 | Zeltinger et al. |
| 7,491,232 B2 | 2/2009 | Bolduc et al. |
| 7,499,756 B2 | 3/2009 | Bowe et al. |
| 7,510,574 B2 | 3/2009 | L et al. |
| 7,524,330 B2 | 4/2009 | Berreklouw |
| 7,530,995 B2 | 5/2009 | Quijano et al. |
| 7,544,206 B2 | 6/2009 | Cohn |
| 7,570,981 B2 | 8/2009 | Peterson |
| 7,601,159 B2 | 10/2009 | Ewers |
| 7,622,276 B2 | 11/2009 | Cunanan et al. |
| 7,628,802 B2 | 12/2009 | White et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,697,984 B2 | 4/2010 | Hill et al. |
| 7,711,421 B2 | 5/2010 | Shafer et al. |
| 7,712,606 B2 | 5/2010 | Salahieh et al. |
| 7,722,638 B2 | 5/2010 | Deyette, Jr. |
| 7,722,662 B2 | 5/2010 | Steinke |
| 7,722,666 B2 | 5/2010 | Lafontaine |
| 7,736,388 B2 | 6/2010 | Goldfarb |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. |
| 7,846,204 B2 | 12/2010 | Letac |
| 7,857,845 B2 | 12/2010 | Stacchino et al. |
| 7,892,292 B2 | 2/2011 | Stack et al. |
| 7,914,574 B2 | 3/2011 | Schmid |
| 7,917,210 B2 | 3/2011 | Baynham et al. |
| 7,918,880 B2 | 4/2011 | Austin |
| 7,927,363 B2 | 4/2011 | Perouse |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,962,208 B2 | 6/2011 | Shuros et al. |
| 7,967,853 B2 | 6/2011 | Eidenschink et al. |

(56) References Cited

U.S. PATENT DOCUMENTS

| | | |
|---|---|---|
| 7,979,123 B2 | 7/2011 | Prinzen et al. |
| 7,988,724 B2 | 8/2011 | Salahieh et al. |
| 8,027,723 B2 | 9/2011 | Pastore et al. |
| 8,036,741 B2 | 10/2011 | Jahns et al. |
| 8,048,153 B2 | 11/2011 | Salahieh et al. |
| 8,052,749 B2 | 11/2011 | Salahieh et al. |
| 8,167,894 B2 | 5/2012 | Miles et al. |
| 8,182,528 B2 | 5/2012 | Salahieh et al. |
| 8,214,040 B2 | 7/2012 | Pastore et al. |
| 8,226,710 B2 | 7/2012 | Nguyen et al. |
| 8,231,670 B2 | 7/2012 | Salahieh |
| 8,244,352 B2 | 8/2012 | Eidenschink et al. |
| 8,246,678 B2 | 8/2012 | Salahieh et al. |
| 8,252,052 B2 | 8/2012 | Salahieh et al. |
| 8,277,500 B2 | 10/2012 | Schmid et al. |
| 8,328,868 B2 | 12/2012 | Paul et al. |
| 8,343,213 B2 | 1/2013 | Salahieh et al. |
| 8,348,999 B2 | 1/2013 | Kheradvar et al. |
| 8,376,865 B2 | 2/2013 | Forster et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,855,762 B2 | 10/2014 | Baynham et al. |
| 8,858,620 B2 | 10/2014 | Salahieh et al. |
| 9,005,273 B2 | 4/2015 | Salahieh et al. |
| 9,037,235 B2 | 5/2015 | Tomaschko et al. |
| 2001/0002445 A1 | 5/2001 | Vesely |
| 2001/0007956 A1 | 7/2001 | Letac et al. |
| 2001/0010017 A1 | 7/2001 | Letac |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026228 A1 | 2/2002 | Schauerte |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042632 A1 | 4/2002 | Iaizzo et al. |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0072777 A1 | 6/2002 | Lu |
| 2002/0077696 A1 | 6/2002 | Zadno-Azizi et al. |
| 2002/0082609 A1 | 6/2002 | Green |
| 2002/0095067 A1 | 7/2002 | Guenst et al. |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0004549 A1 | 1/2003 | Hill et al. |
| 2003/0009189 A1 | 1/2003 | Gilson et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0045908 A1 | 3/2003 | Condie et al. |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060821 A1 | 3/2003 | Hall et al. |
| 2003/0060844 A1 | 3/2003 | Borillo et al. |
| 2003/0060854 A1 | 3/2003 | Zhu |
| 2003/0069492 A1 | 4/2003 | Abrams et al. |
| 2003/0069646 A1 | 4/2003 | Stinson |
| 2003/0070944 A1 | 4/2003 | Nigam |
| 2003/0078471 A1 | 4/2003 | Foley et al. |
| 2003/0100918 A1 | 5/2003 | Duane |
| 2003/0100919 A1 | 5/2003 | Hopkins et al. |
| 2003/0105493 A1* | 6/2003 | Salo .................................. 607/9 |
| 2003/0109901 A1 | 6/2003 | Greatbatch |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125774 A1 | 7/2003 | Salo |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0139778 A1 | 7/2003 | Fischell et al. |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0158583 A1 | 8/2003 | Burnett et al. |
| 2003/0158584 A1 | 8/2003 | Cates et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204206 A1 | 10/2003 | Padua et al. |
| 2003/0204231 A1 | 10/2003 | Hine et al. |
| 2003/0208224 A1 | 11/2003 | Broome |
| 2003/0212361 A1 | 11/2003 | Boyle et al. |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229386 A1 | 12/2003 | Rosenman et al. |
| 2003/0229390 A1 | 12/2003 | Ashton et al. |
| 2003/0233117 A1 | 12/2003 | Adams et al. |
| 2003/0233130 A1 | 12/2003 | Padmanabhan et al. |
| 2004/0010189 A1 | 1/2004 | van Sloun et al. |
| 2004/0015081 A1 | 1/2004 | Kramer et al. |
| 2004/0015204 A1 | 1/2004 | Whitehurst et al. |
| 2004/0019374 A1 | 1/2004 | Hojeibane et al. |
| 2004/0034411 A1 | 2/2004 | Quijano et al. |
| 2004/0038947 A1 | 2/2004 | Wink et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |

(56) References Cited

U.S. PATENT DOCUMENTS

| | | |
|---|---|---|
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088017 A1 | 5/2004 | Sharma et al. |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0106960 A1 | 6/2004 | Siejko et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116994 A1 | 6/2004 | De Bellis |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133247 A1 | 7/2004 | Stahmann et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0162599 A1 | 8/2004 | Kurth |
| 2004/0167565 A1 | 8/2004 | Beulke et al. |
| 2004/0167620 A1 | 8/2004 | Ortiz et al. |
| 2004/0172081 A1 | 9/2004 | Wang |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano |
| 2004/0210307 A1 | 10/2004 | Khairkhahan |
| 2004/0214148 A1 | 10/2004 | Salvino et al. |
| 2004/0215139 A1 | 10/2004 | Cohen |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0255956 A1 | 12/2004 | Vinten-Johansen et al. |
| 2004/0260390 A1 | 12/2004 | Sara |
| 2004/0267326 A1 | 12/2004 | Ocel |
| 2005/0004476 A1 | 1/2005 | Payvar et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0038345 A1 | 2/2005 | Gorgenberg et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075673 A1 | 4/2005 | Warkentin et al. |
| 2005/0075712 A1 | 4/2005 | Biancucci et al. |
| 2005/0075717 A1 | 4/2005 | Nguyen |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull |
| 2005/0085842 A1 | 4/2005 | Eversull |
| 2005/0085843 A1 | 4/2005 | Opolski |
| 2005/0085890 A1 | 4/2005 | Rasmussen |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak |
| 2005/0096735 A1 | 5/2005 | Hojeibane et al. |
| 2005/0096736 A1 | 5/2005 | Osse et al. |
| 2005/0096738 A1 | 5/2005 | Cali |
| 2005/0100580 A1 | 5/2005 | Osborne |
| 2005/0107822 A1 | 5/2005 | WasDyke |
| 2005/0113910 A1 | 5/2005 | Paniagua et al. |
| 2005/0119545 A1 | 6/2005 | Swanson |
| 2005/0131438 A1 | 6/2005 | Cohn et al. |
| 2005/0137483 A1 | 6/2005 | Fischell et al. |
| 2005/0137631 A1 | 6/2005 | Yu et al. |
| 2005/0137647 A1 | 6/2005 | Wallace et al. |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug |
| 2005/0137694 A1 | 6/2005 | Haug |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143780 A1 | 6/2005 | Henry et al. |
| 2005/0143807 A1 | 6/2005 | Pavcnik et al. |
| 2005/0143809 A1 | 6/2005 | Salahieh et al. |
| 2005/0149155 A1 | 7/2005 | Scheiner et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197674 A1 | 9/2005 | McCabe et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0222632 A1 | 10/2005 | Obino |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251239 A1 | 11/2005 | Wallace et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |

(56) References Cited

U.S. PATENT DOCUMENTS

| | | |
|---|---|---|
| 2005/0283962 A1 | 12/2005 | Boudjemline |
| 2005/0288717 A1 | 12/2005 | Sunagawa |
| 2005/0288763 A1 | 12/2005 | Andreas et al. |
| 2006/0004439 A1 | 1/2006 | Spenser et al. |
| 2006/0004442 A1 | 1/2006 | Spenser et al. |
| 2006/0009830 A1 | 1/2006 | Atkinson et al. |
| 2006/0015168 A1 | 1/2006 | Gunderson |
| 2006/0036306 A1 | 2/2006 | Heist et al. |
| 2006/0058597 A1 | 3/2006 | Machado et al. |
| 2006/0058872 A1 | 3/2006 | Salahieh et al. |
| 2006/0100639 A1 | 5/2006 | Levin et al. |
| 2006/0100669 A1 | 5/2006 | Fuimaono et al. |
| 2006/0116593 A1 | 6/2006 | Zhang et al. |
| 2006/0136049 A1 | 6/2006 | Rojo |
| 2006/0142660 A1 | 6/2006 | Maschke |
| 2006/0142812 A1 | 6/2006 | Ortega et al. |
| 2006/0149326 A1 | 7/2006 | Prinzen et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0178586 A1 | 8/2006 | Dobak |
| 2006/0184191 A1 | 8/2006 | O'Brien |
| 2006/0195038 A1 | 8/2006 | Carlson et al. |
| 2006/0195183 A1 | 8/2006 | Navia |
| 2006/0241357 A1 | 10/2006 | Chirife |
| 2006/0241704 A1 | 10/2006 | Shuros et al. |
| 2006/0241733 A1 | 10/2006 | Zhang et al. |
| 2006/0241736 A1 | 10/2006 | Haldeman |
| 2006/0247700 A1 | 11/2006 | Jackson |
| 2006/0253156 A1 | 11/2006 | Pastore et al. |
| 2006/0253191 A1 | 11/2006 | Salahieh et al. |
| 2006/0259085 A1 | 11/2006 | Zhang et al. |
| 2006/0259087 A1 | 11/2006 | Baynham et al. |
| 2006/0259088 A1 | 11/2006 | Pastore et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287684 A1 | 12/2006 | Baynham et al. |
| 2006/0287717 A1 | 12/2006 | Rowe et al. |
| 2006/0293741 A1 | 12/2006 | Johnson et al. |
| 2007/0010876 A1 | 1/2007 | Salahieh |
| 2007/0010877 A1 | 1/2007 | Salahieh et al. |
| 2007/0016286 A1 | 1/2007 | Herrmann et al. |
| 2007/0021789 A1 | 1/2007 | Pastore et al. |
| 2007/0055334 A1 | 3/2007 | Haldeman et al. |
| 2007/0055340 A1 | 3/2007 | Pryor et al. |
| 2007/0061008 A1 | 3/2007 | Salahieh |
| 2007/0088431 A1 | 4/2007 | Bourang et al. |
| 2007/0100410 A1 | 5/2007 | Lamson et al. |
| 2007/0100427 A1 | 5/2007 | Perouse |
| 2007/0112355 A1 | 5/2007 | Salahieh et al. |
| 2007/0118214 A1 | 5/2007 | Salahieh et al. |
| 2007/0150005 A1 | 6/2007 | Sih et al. |
| 2007/0150009 A1 | 6/2007 | Kveen et al. |
| 2007/0162107 A1 | 7/2007 | Haug et al. |
| 2007/0173918 A1 | 7/2007 | Dreher et al. |
| 2007/0203503 A1 | 8/2007 | Salahieh |
| 2007/0233200 A1 | 10/2007 | Maschke |
| 2007/0244552 A1 | 10/2007 | Salahieh et al. |
| 2007/0288089 A1 | 12/2007 | Gurskis |
| 2008/0009940 A1 | 1/2008 | Cribier |
| 2008/0033541 A1 | 2/2008 | Gelbart |
| 2008/0058757 A1 | 3/2008 | Pajunk et al. |
| 2008/0071315 A1 | 3/2008 | Baynham et al. |
| 2008/0071363 A1 | 3/2008 | Tuval et al. |
| 2008/0082136 A1 | 4/2008 | Gaudiani |
| 2008/0082165 A1 | 4/2008 | Wilson et al. |
| 2008/0109063 A1 | 5/2008 | Hancock et al. |
| 2008/0114408 A1 | 5/2008 | Shuros et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere |
| 2008/0234814 A1 | 9/2008 | Salahieh et al. |
| 2008/0269878 A1 | 10/2008 | Lobbi |
| 2008/0288030 A1 | 11/2008 | Zhang et al. |
| 2008/0288054 A1 | 11/2008 | Pulnev et al. |
| 2008/0319502 A1 | 12/2008 | Sunagawa et al. |
| 2009/0005845 A1 | 1/2009 | David et al. |
| 2009/0005863 A1 | 1/2009 | Goetz et al. |
| 2009/0030512 A1 | 1/2009 | Thielen et al. |
| 2009/0054969 A1 | 2/2009 | Salahieh |
| 2009/0076598 A1 | 3/2009 | Salahieh et al. |
| 2009/0143835 A1 | 6/2009 | Pastore et al. |
| 2009/0171456 A1 | 7/2009 | Kveen |
| 2009/0222076 A1 | 9/2009 | Figulla et al. |
| 2009/0264997 A1 | 10/2009 | Salahieh |
| 2009/0299462 A1 | 12/2009 | Fawzi |
| 2009/0318943 A1 | 12/2009 | Eidenschink et al. |
| 2009/0318984 A1 | 12/2009 | Mokelke et al. |
| 2009/0318989 A1 | 12/2009 | Tomaschko et al. |
| 2009/0318990 A1 | 12/2009 | Tomaschko et al. |
| 2009/0318991 A1 | 12/2009 | Tomaschko et al. |
| 2009/0318992 A1 | 12/2009 | Eidenschink et al. |
| 2009/0318993 A1 | 12/2009 | Eidenschink et al. |
| 2009/0318994 A1 | 12/2009 | Eidenschink et al. |
| 2010/0056858 A1 | 3/2010 | Mokelke et al. |
| 2010/0094399 A1 | 4/2010 | Dorn et al. |
| 2010/0121434 A1 | 5/2010 | Paul et al. |
| 2010/0130913 A1 | 5/2010 | Baynham et al. |
| 2010/0219092 A1 | 9/2010 | Salahieh |
| 2010/0280495 A1 | 11/2010 | Paul et al. |
| 2011/0137363 A1 | 6/2011 | Baynham et al. |
| 2011/0144709 A1 | 6/2011 | Baynham et al. |
| 2011/0230928 A1 | 9/2011 | Shuros et al. |
| 2011/0257735 A1 | 10/2011 | Salahieh et al. |
| 2011/0288634 A1 | 11/2011 | Tuval et al. |
| 2012/0022642 A1 | 1/2012 | Haug et al. |
| 2012/0029627 A1 | 2/2012 | Salahieh et al. |
| 2012/0041550 A1 | 2/2012 | Salahieh et al. |
| 2012/0053683 A1 | 3/2012 | Salahieh et al. |
| 2012/0089224 A1 | 4/2012 | Haug |
| 2012/0303113 A1 | 11/2012 | Benichou |
| 2012/0330409 A1 | 12/2012 | Haug et al. |
| 2013/0018457 A1 | 1/2013 | Gregg |
| 2013/0123898 A1 | 5/2013 | Tung et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | | |
|---|---|---|---|
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 103546 | A1 | 3/1984 |
| EP | 144167 | A2 | 6/1985 |
| EP | 0597967 | B1 | 5/1994 |
| EP | 0409929 | B1 | 4/1997 |
| EP | 0819013 | A1 | 1/1998 |
| EP | 0850607 | A1 | 7/1998 |
| EP | 1000590 | A1 | 5/2000 |
| EP | 1057459 | A1 | 12/2000 |
| EP | 1057460 | A1 | 12/2000 |
| EP | 1088529 | A2 | 4/2001 |
| EP | 937439 | B1 | 9/2003 |
| EP | 1340473 | A2 | 9/2003 |
| EP | 1356793 | A2 | 10/2003 |
| EP | 1042045 | B1 | 5/2004 |
| EP | 1430853 | A2 | 6/2004 |
| EP | 1435879 | A1 | 7/2004 |

(56) References Cited

FOREIGN PATENT DOCUMENTS

| | | | |
|---|---|---|---|
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551336 A1 | 7/2005 |
| EP | 1078610 B1 | 8/2005 |
| EP | 1562515 A1 | 8/2005 |
| EP | 1576937 A2 | 9/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1690566 A1 | 8/2006 |
| EP | 1605871 B1 | 7/2008 |
| EP | 1570809 B1 | 1/2009 |
| EP | 1551274 B1 | 12/2014 |
| FR | 2788217 A1 | 7/2000 |
| GB | 2056023 A | 3/1981 |
| GB | 2398245 A | 8/2004 |
| JP | 5245215 A | 9/1993 |
| JP | 7504597 A | 5/1995 |
| JP | 2002514478 A | 5/2002 |
| JP | 2004533297 A | 11/2004 |
| JP | 2006516451 A | 7/2006 |
| JP | 2011524787 A | 9/2011 |
| WO | WO-91/17720 A1 | 11/1991 |
| WO | WO-92/17118 A1 | 10/1992 |
| WO | WO-93/01768 A1 | 2/1993 |
| WO | WO-93/15693 A1 | 8/1993 |
| WO | WO-95/04556 A2 | 2/1995 |
| WO | WO-9518649 A1 | 7/1995 |
| WO | WO-95/29640 A1 | 11/1995 |
| WO | WO-96/14032 A1 | 5/1996 |
| WO | WO-96/24306 A1 | 8/1996 |
| WO | WO-96/40012 A1 | 12/1996 |
| WO | WO-98/29057 A1 | 7/1998 |
| WO | WO-98/36790 A1 | 8/1998 |
| WO | WO-98/50103 A1 | 11/1998 |
| WO | WO-98/57599 A2 | 12/1998 |
| WO | WO-99/33414 A1 | 7/1999 |
| WO | WO-99/40964 A1 | 8/1999 |
| WO | WO-99/44542 A2 | 9/1999 |
| WO | WO-99/47075 A1 | 9/1999 |
| WO | WO-9958191 A1 | 11/1999 |
| WO | WO-00/09059 A2 | 2/2000 |
| WO | WO-00/41652 A1 | 7/2000 |
| WO | WO-00/44308 A2 | 8/2000 |
| WO | WO-00/44311 A2 | 8/2000 |
| WO | WO-00/44313 A1 | 8/2000 |
| WO | WO-00/45874 A1 | 8/2000 |
| WO | WO-00/47139 A1 | 8/2000 |
| WO | WO-00/49970 A1 | 8/2000 |
| WO | WO-00/67661 A2 | 11/2000 |
| WO | WO-01/05331 A1 | 1/2001 |
| WO | WO-01/08596 A1 | 2/2001 |
| WO | WO-01/10320 A1 | 2/2001 |
| WO | WO-01/10343 A1 | 2/2001 |
| WO | WO-0115609 A1 | 3/2001 |
| WO | WO-01/35870 A1 | 5/2001 |
| WO | WO-01/49213 A2 | 7/2001 |
| WO | WO-01/54625 A1 | 8/2001 |
| WO | WO-01/62189 A1 | 8/2001 |
| WO | WO-01/64137 A1 | 9/2001 |
| WO | WO-01/97715 A1 | 12/2001 |
| WO | WO-02/36048 A1 | 5/2002 |
| WO | WO-02/41789 A2 | 5/2002 |
| WO | WO-02/43620 A1 | 6/2002 |
| WO | WO-02/47575 A2 | 6/2002 |
| WO | WO-02/100297 A2 | 12/2002 |
| WO | WO-03/003943 A2 | 1/2003 |
| WO | WO-03/003949 A2 | 1/2003 |
| WO | WO-03/011195 A2 | 2/2003 |
| WO | WO-03/015851 A1 | 2/2003 |
| WO | WO-03/028592 A1 | 4/2003 |
| WO | WO-03/030776 A2 | 4/2003 |
| WO | WO-03/037227 A2 | 5/2003 |
| WO | WO-03035139 A1 | 5/2003 |
| WO | WO-03/094793 A1 | 11/2003 |
| WO | WO-03/094797 A1 | 11/2003 |
| WO | WO-2004/014256 A1 | 2/2004 |
| WO | WO-2004/019811 A2 | 3/2004 |
| WO | WO-2004/023980 A2 | 3/2004 |
| WO | WO-2004/026117 A2 | 4/2004 |
| WO | WO-2004/041126 A1 | 5/2004 |
| WO | WO-2004/047681 A1 | 6/2004 |
| WO | WO-2004/058106 A2 | 7/2004 |
| WO | WO-2004058326 A1 | 7/2004 |
| WO | WO-2004058326 A2 | 7/2004 |
| WO | WO-2004/066876 A1 | 8/2004 |
| WO | WO-2004/082536 A1 | 9/2004 |
| WO | WO-2004/089250 A1 | 10/2004 |
| WO | WO-2004/089253 A1 | 10/2004 |
| WO | WO-2004/093728 A2 | 11/2004 |
| WO | WO-2004096290 A1 | 11/2004 |
| WO | WO-2004/105651 A1 | 12/2004 |
| WO | WO 2005//002466 A2 | 1/2005 |
| WO | WO-2005/004753 A1 | 1/2005 |
| WO | WO-2005000206 A2 | 1/2005 |
| WO | WO-2005/009285 A2 | 2/2005 |
| WO | WO-2005/011534 A1 | 2/2005 |
| WO | WO 2005/011535 A2 | 2/2005 |
| WO | WO-2005/023155 A1 | 3/2005 |
| WO | WO-2005/027790 A1 | 3/2005 |
| WO | WO-2005/046528 A1 | 5/2005 |
| WO | WO-2005/046529 A1 | 5/2005 |
| WO | WO-2005042083 A2 | 5/2005 |
| WO | WO-2005/048883 A1 | 6/2005 |
| WO | WO-2005/062980 A2 | 7/2005 |
| WO | WO-2005/065585 A1 | 7/2005 |
| WO | WO-2005065771 A1 | 7/2005 |
| WO | WO-2005/084595 A1 | 9/2005 |
| WO | WO-2005/087140 A1 | 9/2005 |
| WO | WO-2005/096993 A1 | 10/2005 |
| WO | WO-2006/009690 A1 | 1/2006 |
| WO | WO-2006/027499 A2 | 3/2006 |
| WO | WO-2006060586 A1 | 6/2006 |
| WO | WO-2006115693 A2 | 11/2006 |
| WO | WO-2006115693 A3 | 11/2006 |
| WO | WO-2006/124636 A2 | 11/2006 |
| WO | WO-2006/124636 A3 | 11/2006 |
| WO | WO-2006/124729 A2 | 11/2006 |
| WO | WO-2006/124729 A3 | 11/2006 |
| WO | WO-2006/138391 A2 | 12/2006 |
| WO | WO-2007/033093 A2 | 3/2007 |
| WO | WO-2007/035471 A2 | 3/2007 |
| WO | WO-2007/044285 A2 | 4/2007 |
| WO | WO-2007/053243 A2 | 5/2007 |
| WO | WO-2007/058847 A2 | 5/2007 |
| WO | WO-2007/092354 A2 | 8/2007 |
| WO | WO-2007/097983 A2 | 8/2007 |
| WO | WO-2007133962 A2 | 11/2007 |
| WO | WO-2007133962 A3 | 11/2007 |
| WO | WO-2008027261 A1 | 3/2008 |
| WO | WO-2009154720 A1 | 12/2009 |
| WO | WO-2009154730 A1 | 12/2009 |
| WO | WO-2010/042950 A2 | 4/2010 |

OTHER PUBLICATIONS

"U.S. Appl. No. 11/030,575, Response filed Oct. 26, 2006 to Non Final Office Action mailed Jul. 26, 2006", 8 pgs.

"U.S. Appl. No. 11/113,828, Advisory Action mailed Feb. 2, 2010", 3 pgs.

"U.S. Appl. No. 11/113,828, Examiner Interview Summary mailed Feb. 4, 2011", 1 pg.

"U.S. Appl. No. 11/113,828, Final Office Action mailed Jun. 29, 2009", 11 pgs.

"U.S. Appl. No. 11/113,828, Final Office Action mailed Sep. 17, 2008", 10 pgs.

"U.S. Appl. No. 11/113,828, Final Office Action mailed Nov. 24, 2009", 13 pgs.

(56) References Cited

OTHER PUBLICATIONS

"U.S. Appl. No. 11/113,828, Non Final Office Action mailed Mar. 5, 2008", 8 pgs.
"U.S. Appl. No. 11/113,828, Non Final Office Action mailed Dec. 22, 2008", 10 pgs.
"U.S. Appl. No. 11/113,828, Notice of Allowance mailed Feb. 4, 2011", 7 pgs.
"U.S. Appl. No. 11/113,828, Notice of Allowance mailed Oct. 19, 2010", 4 pgs.
"U.S. Appl. No. 11/113,828, Response filed Jan. 25, 2010 to Final Office Action mailed Nov. 24, 2009", 8 pgs.
"U.S. Appl. No. 11/113,828, Response filed Jan. 28, 2008 to Restriction Requirement mailed Dec. 26, 2007", 7 pgs.
"U.S. Appl. No. 11/113,828, Response filed Mar. 23, 2009 to Non Final Office Action mailed Dec. 22, 2008", 8 pgs.
"U.S. Appl. No. 11/113,828, Response filed Jun. 5, 2008 to Non Final Office Action mailed Mar. 5, 2008", 8 pgs.
"U.S. Appl. No. 11/113,828, Response filed Oct. 29, 2009 to Final Office Action mailed Jun. 29, 2009", 9 pgs.
"U.S. Appl. No. 11/113,828, Response filed Nov. 17, 2008 to Final Office Action mailed Sep. 17, 2008", 11 pgs.
"U.S. Appl. No. 11/113,828, Restriction Requirement mailed Dec. 26, 2007", 8 pgs.
"U.S. Appl. No. 11/129,050, Advisory Action mailed Jul. 14, 2009", 3 pgs.
"U.S. Appl. No. 11/129,050, Examiner Interview Summary mailed Feb. 11, 2009", 2 pgs.
"U.S. Appl. No. 11/129,050, Final Office Action mailed Apr. 21, 2009", 10 pgs.
"U.S. Appl. No. 11/129,050, Final Office Action mailed May 12, 2008", 8 pgs.
"U.S. Appl. No. 11/129,050, Non Final Office Action mailed Nov. 6, 2008", 7 pgs.
"U.S. Appl. No. 11/129,050, Non Final Office Action mailed Nov. 26, 2007", 7 pgs.
"U.S. Appl. No. 11/129,050, Notice of Allowance mailed Apr. 1, 2010", 6 pgs.
"U.S. Appl. No. 11/129,050, Notice of Allowance mailed Jul. 16, 2010", 4 pgs.
"U.S. Appl. No. 11/129,050, Notice of Allowance mailed Aug. 24, 2009", 7 pgs.
"U.S. Appl. No. 11/129,050, Notice of Allowance mailed Dec. 2, 2009", 4 pgs.
"U.S. Appl. No. 11/129,050, Response filed Feb. 23, 2009 to Non Final Office Action mailed Nov. 6, 2008", 13 pgs.
"U.S. Appl. No. 11/129,050, Response filed Feb. 26, 2008 to Non Final Office Action mailed Nov. 26, 2007", 14 pgs.
"U.S. Appl. No. 11/129,050, Response filed Jun. 22, 2009 to Final Office Action mailed Apr. 21, 2009", 9 pgs.
"U.S. Appl. No. 11/129,050, Response filed Jul. 14, 2008 to Final Office Action mailed May 12, 2008", 13 pgs.
"U.S. Appl. No. 11/129,050, Response filed Sep. 28, 2007 to Restriction Requirement mailed Aug 1, 2007", 11 pgs.
"U.S. Appl. No. 11/129,050, Supplemental Response filed Sep. 12, 2008 to Final Office Action mailed May 12, 2008", 12 pgs.
"U.S. Appl. No. 11/129,058, Advisory Action mailed Oct. 17, 2007", 3 pgs.
"U.S. Appl. No. 11/129,058, Appeal Brief filed Jan. 8, 2008", 23 pgs.
"U.S. Appl. No. 11/129,058, Examiner's Answer to Appeal Brief mailed Jun. 18, 2008", 14 pgs.
"U.S. Appl. No. 11/129,058, Final Office Action mailed Jul. 9, 2007", 12 pgs.
"U.S. Appl. No. 11/129,058, Non Final Office Action mailed Jan. 29, 2007", 11 pgs.
"U.S. Appl. No. 11/129,058, Office Communication mailed Jan. 15, 2010", 2 pgs.
"U.S. Appl. No. 11/129,058, Response filed Apr. 30, 2007 to Non Final Office Action mailed Jan. 29, 2007", 16 pgs.
"U.S. Appl. No. 11/129,058, Response filed Oct. 9, 2007 to Final Office Action mailed Jul. 9, 2007", 14 pgs.

"U.S. Appl. No. 11/382,849, Final Office Action mailed Jan. 28, 2010", 7 pgs.
"U.S. Appl. No. 11/382,849, Non-Final Office Action mailed May 12, 2010", 5 pgs.
"U.S. Appl. No. 11/382,849, Non-Final Office Action mailed Aug. 31, 2009", 8 pgs.
"U.S. Appl. No. 11/382,849, Response filed Apr. 26, 2010 to Final Office Action mailed Jan. 28, 2010", 10 pgs.
"U.S. Appl. No. 11/382,849, Response filed Jun. 8, 2009 to Restriction Requirement mailed May 6, 2009", 8 pgs.
"U.S. Appl. No. 11/382,849, Response filed Aug. 2, 2010 to Non Final Office Action mailed May 12, 2010", 7 pgs.
"U.S. Appl. No. 11/382,849, Response filed Nov. 30, 2009 to Non Final Office Action mailed Aug. 31, 2009", 11 pgs.
"U.S. Appl. No. 11/382,849, Restriction Requirement mailed May 6, 2009", 6 pgs.
"U.S. Appl. No. 11/468,875, Advisory Action mailed Aug. 19, 2009", 3 pgs.
"U.S. Appl. No. 11/468,875, Final Office Action mailed Jun. 1, 2009", 6 pgs.
"U.S. Appl. No. 11/468,875, Non-Final Office Action mailed Dec. 11, 2008", 8 pgs.
"U.S. Appl. No. 11/468,875, Response filed Mar. 9, 2009 to Non-Final Office Action mailed Dec. 11, 2008", 10 pgs.
"U.S. Appl. No. 11/468,875, Response filed Aug. 3, 2009 to Final Office Action mailed Jun. 1, 2009", 8 pgs.
"U.S. Appl. No. 11/468,875, Response filed Sep. 1, 2009 to Advisory Action mailed Aug. 19, 2009 and the Final Office Action mailed Jun. 1, 2009", 9 pgs.
"U.S. Appl. No. 11/868,767, Notice of Allowance mailed Mar. 24, 2010", 7 pgs.
"U.S. Appl. No. 11/868,767, Notice of Allowance mailed Sep. 17, 2010", 4 pgs.
"U.S. Appl. No. 12/322,382, Advisory Action mailed Nov. 8, 2011", 3 pgs.
"U.S. Appl. No. 12/322,382, Final Office Action mailed Aug. 25, 2011", 12 pgs.
"U.S. Appl. No. 12/322,382, Non Final Office Action mailed Mar. 21, 2011", 14 pgs.
"U.S. Appl. No. 12/322,382, Response filed Jun. 21, 2011 to Non Final Office Action mailed Mar. 21, 2011", 16 pgs.
"U.S. Appl. No. 12/322,382, Response filed Oct. 24, 2011 to Final Office Action mailed Aug. 25, 2011", 15 pgs.
"U.S. Appl. No. 12/484,727, Non Final Office Action mailed Feb. 13, 2012", 7 pgs.
"U.S. Appl. No. 12/484,727, Response filed Jan. 23, 2012 to Restriction Requirement mailed Dec. 23, 2011", 6 pgs.
"U.S. Appl. No. 12/484,727, Response filed Jun. 12, 2012 to Non Final Office Action mailed Feb. 13, 2012", 10 pgs.
"U.S. Appl. No. 12/484,727, Restriction Requirement mailed Dec. 23, 2011", 7 pgs.
"U.S. Appl. No. 12/484,804, Final office Action mailed Jun. 5, 2012", 10 pgs.
"U.S. Appl. No. 12/484,804, Response filed May 3, 2012 to Non-Final Office Action mailed Feb. 6, 2012", 12 pgs.
"U.S. Appl. No. 12/484,804, Response filed Dec. 14, 2011 to Restriction Requirement mailed Nov. 14, 2011", 7 pgs.
"U.S. Appl. No. 12/484,804, Restriction Requirement mailed Nov. 14, 2011", 8 pgs.
"U.S. Appl. No. 12/484,804. Non Final Office Action Mailed Feb. 6, 2012", 8 pgs.
"U.S. Appl. No. 12/694,328 , Response filed Oct. 19, 2011 to Non Final Office Action mailed Aug. 19, 2011", 13 pgs.
"U.S. Appl. No. 12/694,328 , Response filed Nov. 21, 2011 to Advisory Action mailed Oct. 28, 2011 and Non Final Office Action mailed Aug. 19, 2011", 13 pgs.
"U.S. Appl. No. 12/694,328, Advisory Action mailed Oct. 28, 2011", 3 pgs.
"U.S. Appl. No. 12/694,328, Final Office Action mailed Aug. 19, 2011", 12 pgs.
"U.S. Appl. No. 12/694,328, Non Final Office Action mailed Feb. 8, 2011", 13 pgs.

(56) References Cited

OTHER PUBLICATIONS

"U.S. Appl. No. 12/694,328, Response filed Jun. 8, 2011 to Non Final Office Action mailed Feb. 8, 2011", 12 pgs.
"U.S. Appl. No. 13/029,631, Notice of Allowance mailed Aug. 24, 2012", 7 pgs.
"U.S. Appl. No. 13/113,706 , Response filed Jan. 9, 2013 to Non Final Office Action mailed Oct. 12, 2012", 6 pgs.
"U.S. Appl. No. 13/113,706, Non Final Office Action mailed Oct. 12, 2012", 4 pgs.
"U.S. Appl. No. 13/113,706, Non Final Office Action Mailed Dec. 21, 2011", 6 pgs.
"U.S. Appl. No. 13/113,706, Notice of Allowance mailed Jan. 31, 2013", 7 pgs.
"U.S. Appl. No. 13/113,706, Response filed Mar. 21, 2012 to Non Final Office Action mailed Dec. 21, 2011", 14 pgs.
"Arrow Bipolar Pacing Catheters and Pacing Kits", Arrow International, (2000), 4 pgs.
"Australian Application Serial No. 2007290672, First Examiner Report Received mailed Aug. 23, 2010", 2 pgs.
"Australian Application Serial No. 2007290672, Response filed Mar. 17, 2011 to Non Final Office Action mailed Aug. 23, 2010", 11.
"Chinese Application Serial No. 200780032286.X, Office Action mailed Feb. 13, 2012", (English Translation), 5 pgs.
"Chinese Application Serial No. 200780032286.X, Response filed Jun. 28, 2011 to Non Final Office Action dated Feb. 23, 2011", (w/ English Translation), 15 pgs.
"Chinese Application Serial No. 200780032286.X, Office Action mailed Feb. 23, 2011", 5 pgs.
"Coronary Dilatation Catheters", online]. [archived Mar. 3, 2006]. Retrieved from the Internet: <URL: http://web.archive.org/web/20060303151627/http://www.guidant.com/products/TemplatePDFs/NoPriceDilataticatheters.pdf>, (2006), 3 pgs.
"European Application Serial No. 06740227.1, Communication dated Dec. 27, 2007", 2 pgs.
"European Application Serial No. 06740227.1, Office Action mailed Mar. 10, 2011", 4 pgs.
"European Application Serial No. 06740227.1, Response filed Jan. 27, 2008 to Communication dated Dec. 27, 2007", 9 pgs.
"European Application Serial No. 06740227.1, Response filed Jul. 12, 2011 to Office Action dated Mar. 10, 2011", 15 pgs.
"European Application Serial No. 06752527.9, Communication mailed Mar. 8, 2010", 6 pgs.
"European Application Serial No. 06752527.9, Response filed Jul. 7, 2010 to Office Action dated Mar. 8, 2010", 15 pgs.
"European Application Serial No. 06752527.9, Summons to Attend Oral Proceedings Received mailed Jul. 23, 2010", 3 pgs.
"European Application Serial No. 06752540.2, Communication Mar. 3, 2008", 2 pgs.
"European Application Serial No. 06752540.2, Communication mailed Mar. 8, 2010", 2 pgs.
"European Application Serial No. 06752540.2, Response filed Apr. 9, 2008 to Communication Mar. 3, 2008", 6 pgs.
"European Application Serial No. 06752540.2, Response filed Jul. 15, 2010 to Communication mailed Mar. 8, 2010", 20 pgs.
"European Application Serial No. 06762527.9, Communication pursuant to Rules 161 to 182 EPC mailed Mar. 3, 2008", 2 pgs.
"European Application Serial No. 06762527.9, Response filed Apr. 9, 2008 to Communication pursuant to Rules 161 to 182 EPC mailed Mar. 3, 2008", 6 pgs.
"European Application Serial No. 07797336.0, Communication mailed Mar. 10, 2010", 3 pgs.
"European Application Serial No. 07797336.0, Office Action mailed Feb. 24, 2009", 4 pgs.
"European Application Serial No. 07797336.0, Response filed Jul. 6, 2009 to Communication mailed Feb. 24, 2009", 20 pgs.
"European Application Serial No. 07797336.0, Response filed Jul. 7, 2010 to Office Action dated Mar. 10, 2010", 5 pgs.
"European Application Serial No. 07837205.9, Communication dated Apr. 8, 2009", 2 pgs.
"European Application Serial No. 09767033.5, Office Action mailed Apr. 15, 2011", 1 pg.
"European Application Serial No. 09767033.5, Response filed May 18, 2011 to Office Action mailed Apr. 15, 2011", 7 pgs.
"European Application Serial No. 09767033.5, Response filed Dec. 5, 2011 to Office Action mailed Aug. 2, 2011", 10 pgs.
"European Application Serial No. 09767043.4, Office Action mailed Apr. 14, 2011", 1 pg.
"European Application Serial No. 09767043.4, Response filed May 24, 2011 to Office Action mailed Apr. 14, 2011", 13 pgs.
"European Application Serial No. 09767033.5, Examination Notification Art. 94(3) mailed Aug. 2, 2011", 6 pgs.
"Guidant Product Catalog", [online]. [archived Feb. 4, 2005]. Retrieved from the Internet: <URL: http://web.archive.org/web/20050204225345/http://guidant.com/products/VIproductcatalog.pdf>, (2005), 133 pgs.
"International Application Serial No. PCT/US/2009/003589, International Search Report mailed Sep. 14, 2009", 5 pgs.
"International Application Serial No. PCT/US2006/018497, International Search Report mailed Oct. 24, 2006", 5 pgs.
"International Application Serial No. PCT/US2006/018497, Written Opinion mailed Oct. 24, 2006", 7 pgs.
"International Application Serial No. PCT/US2006/018642, International Search Report and Written Opinion mailed Oct. 24, 2006", 14 pgs.
"International Application Serial No. PCT/US2006/018642, International Search Report mailed Oct. 24, 2006", 5 pgs.
"International Application Serial No. PCT/US2006/018642, Written Opinion mailed Oct. 24, 2006", 7 pgs.
"International Application Serial No. PCT/US2007/018577, International Search Report mailed Jan. 15, 2008", 4 pgs.
"International Application Serial No. PCT/US2007/018577, Written Opinion mailed Jan. 15, 2008", 7 pgs.
"International Application Serial No. PCT/US2007/068217, International Search Report mailed Oct. 30, 2007", 5 pgs.
"International Application Serial No. PCT/US2007/068217, Written Opinion mailed Oct. 30, 2007", 8 pgs.
"International Application Serial No. PCT/US2009/003575, International Search Report mailed Sep. 14, 2009", 6 pgs.
"International Application Serial No. PCT/US2009/003575, Written Opinion mailed Sep. 14, 2009", 9 pgs.
"International Application Serial No. PCT/US2009/003577, International Preliminary Report on Patentability mailed Jan. 6, 2011", 12 pgs.
"International Application Serial No. PCT/US2009/003577, International Search Report mailed Aug. 9, 2009", 5 pgs.
"International Application Serial No. PCT/US2009/003577, Written Opinion mailed Aug. 9, 2009", 10 pgs.
"International Application Serial No. PCT/US2009/003581, International Search Report mailed Sep. 21, 2009", 5 pgs.
"International Application Serial No. PCT/US2009/003581, Written Opinion mailed Sep. 21, 2009", 10 pgs.
"International Application Serial No. PCT/US2009/003589, Written Opinion mailed Sep. 14, 2009", 11 pgs.
"International Application Serial No. PCT/US2009/003590, International Preliminary Report on Patentability mailed Jan. 6, 2011", 9 pgs.
"International Application Serial No. PCT/US2009/003590, International Search Report mailed Sep. 14, 2009", 5 pgs.
"International Application Serial No. PCT/US2009/003590, Written Opinion mailed Sep. 14, 2009", 10 pgs.
"International Application Serial No. PCT/US2009/003594, International Search Report mailed Sep. 17, 2009", 5 pgs.
"International Application Serial No. PCT/US2009/003594, Written Opinion mailed Sep. 17, 2009", 9 pgs.
"International Search Report and Written Opinion for Application No. PCT/US2006/011972 mailed Oct. 6, 2006", 16 pgs.
"Japanese Application Serial No. 2008-508872, Office Action mailed Oct. 27, 2011", 6 pgs.
"Japanese Application Serial No. 2008-508872, Response filed Jan. 31, 2012 to Office Action mailed Oct. 31, 2011", W/English Translation, 14 pgs.

(56) References Cited

OTHER PUBLICATIONS

"Japanese Application Serial No. 2008-511421, Office Action mailed Nov. 16, 2011", (w/ English Translation), 5 pgs.
"Japanese Application Serial No. 2008-511421, Voluntary Amendment filed Apr. 27, 2009", (w/ English Translation of Amended Claims), 11 pgs.
"Japanese Application Serial No. 2008-511452, Office Action mailed Nov. 14, 2011", 4 pgs.
"Japanese Application Serial No. 2008-511452, Response filed Feb. 14, 2012 to Office Action mailed Nov. 14, 2011", (English Translation of Claims), 3 pgs.
"Japanese Application Serial No. 2008-511452, Voluntary Amendment filed May 11, 2009", (w/ English Translation of Amended Claims), 8 pgs.
"Japanese Application Serial No. 2009-510093, Voluntary Amendment filed Jan. 14, 2009", 4 pgs.
"Japanese Application Serial No. 2011-514591, Voluntary Amendment filed Jan. 12, 2011", (w/ English Translation), 11 pgs.
"Japanese Application Serial No. 2011-514594, Voluntary Amendment filed Jan. 18, 2011", (w/ English Translation of Amended Claims), 49 pgs.
"Product Overview: RX ACCULINK Carotid Stent System; RX ACCUNET Embolic Protection System", [online]. [retrieved Apr. 14, 2006]. Retrieved from the Internet: <URL: http://web.archive.org/web/20060414151850/http://www.guidant.com/webapp/emarketing/ppt/acculink/ACCULINK.pdf>, (2005), 23 pgs.
"RX ACCUNET Embolic Protection System", [online]. [retrieved Jan. 11, 2006]. Retrieved from the Internet: <URL:http://www.guidant.com/products/ProductTemplates/ES/accunet.shtml>, (2006), 4 pgs.
"RX ACCUNET Embolic Protection System: Information for Prescribers", [online]. [archived Feb. 5, 2005]. Retrieved from the Internet: <URL: http://web.archive.org/web/20050205044138/http://guidant.com/products/TemplatePDFs/ACCUNET_RX.pdf, (Jan. 6, 2005), 32 pgs.
"VOYAGER RX Coronary Dilatation Catheter", [online]. [retrieved Jan. 11, 2006]. Retrieved from the Internet: <URL: http://www.guidant.com/products/ProductTemplates/VI/RX_US_Voyager_Intro.shtml>, (2006), 2 pgs.
Airaksinen, K. E., et al., "Antiarrhythmic effect of repeated coronary occlusion during balloon angioplasty", J Am Coll Cardiol., 29(5), (Apr. 1997), 1035-1038.
Brockway, Marina V, et al., "Method and Apparatus for Delivering Chronic and Post-Ischemia Cardiac Therapies", U.S. Appl. No. 11/207,251, filed Aug. 19, 2005, 40 pgs.
Girouard, Steven D., "Pulmonary Vein Stent for Treating Atrial Fibrillation", U.S. Appl. No. 60/298,741, filed Jun. 15, 2001, 14 pgs.
Heinroth, K. M, et al., "Temporary transcoronary pacing by coated guidewires", Clin Res Cardiol., 95, (2006), 1-6.
Henriques, Jose P., et al., "Outcome of primary angioplasty for acute myocardial infarction during routine duty hours versus during off-hours", J Am Coll Cardiol, 41(12), (Jun. 18, 2003), 2138-2142.
Kin, Hajime, et al., "Postconditioning attenuates myocardial ischemia-reperfusion injury by inhibiting events in the early minutes of reperfusion", Cardiovascular Research, 62(1), (Apr. 1, 2004), 74-85.
Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.
Koning, M M, "Rapid ventricular pacing produces myocardial protection by nonischemic activation of KATP+ channels", Circulation, 93(1), (Jan. 1, 1996), 178-186.
Meier, B., et al., "Coronary Pacing During Percutaneous Transluminal Coronary Angioplasty", Circulation, 71(3), (Mar. 1985), 557-561.
Murry, C. E., et al., "Preconditioning with ischemia: a delay of lethal cell injury in ischemic myocardium", Circulation, 74(5), (1986), 1124-1136.

Ovize, M., et al., "Stretch preconditions canine myocardium.", Am J Physiol., 266(1 Pt 2), (Jan. 1994), 137-46.
Pastore, Joseph M, et al., "Intermittent Stress Augmentation Pacing for Cardioprotective Effect", U.S. Appl. No. 11/458,286, filed 078-18-06, 23 pgs.
Rosa, A., et al., "Ectopic Pacing at Physiological Rate Improves Postanoxic Recovery of the Developing Heart", Am. J. Physiol.—Heart Circ. Physiol., 284, (2003), 2384-2392.
Tsang, A., et al., "Postconditioning: a form of "modified reperfusion" protects the myocardium by activating the phosphatidylinositol 3-kinase-Akt pathway", Circ Res., 95(3), Epub Jul. 8, 2004, (Aug. 6, 2004), 230-2.
Vanagt, W. Y. R., et al., "Ventricular Pacing for Improving Myocardial Tolerance to Ischemia", Progress Report on Project Guidant-CARIM, (Oct. 2003), 1-25.
Vegh, A, et al., "Transient ischaemia induced by rapid cardiac pacing results in myocardial preconditioning", Cardiovascular Research, 25(12), (Dec. 1991), 1051-3.
Wu, Zhong-Kai, et al., "Ischemic preconditioning suppresses ventricular tachyarrhythmias after myocardial revascularization", Circulation, 106(24), (Dec. 10, 2002), 3091-3096.
Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.
Zhao, et al., "Inhibition of myocardial injury by ischemic postconditioning during reperfusion: comparison with ischemic preconditioning", Am J Physiol Heart Circ Physiol, 285(2), (Aug. 2003), H579-H588.
"U.S. Appl. No. 12/322,382, Non Final Office Action mailed Aug. 26, 2013", 14 pgs.
"U.S. Appl. No. 12/322,382, Response filed Nov. 26, 2013 to Non Final Office Action mailed Aug. 26, 2013", 15 pgs.
"U.S. Appl. No. 13/721,796, Non Final Office Action mailed May 3, 2013", 7 pgs.
"U.S. Appl. No. 13/721,796, Non Final Office Action mailed Oct. 23, 2013", 7 pgs.
"U.S. Appl. No. 12/322,382, Examiner Interview Sumary mailed Jul. 22, 2017", 2 pgs.
"U.S. Appl. No. 12/322,382, Final Office Action mailed Jan. 8, 2014", 15 pgs.
"U.S. Appl. No. 12/694,328, Non Final Office Action mailed Mar. 24, 2014", 15 pgs.
"U.S. Appl. No. 12/694,328, Response filed Jul. 22, 2014 to Non Final Office Action mailed Mar. 24, 2014", 11 pgs.
"U.S. Appl. No. 13/721,796, Final Office Action mailed Apr. 3, 2014", 7 pgs.
"U.S. Appl. No. 13/721,796, Notice of Allowance mailed Jun. 3, 2014", 8 pgs.
"U.S. Appl. No. 13/721,796, Response filed Jan. 21, 2014 to Non Final Office Action mailed Oct. 23, 2013", 10 pgs.
"U.S. Appl. No. 13/721,796, Response filed Apr. 25, 2014 to Final Office Action mailed Apr. 3, 2014", 7 pgs.
"U.S. Appl. No. 12/484,727, Non Final Office Action mailed Oct. 6, 2014", 11 pgs.
"U.S. Appl. No. 12/484,727, Notice of Allowance mailed Jan. 15, 2015", 5 pgs.
"U.S. Appl. No. 12/484,727, Response filed Dec. 16, 2014 to Non Final Office Action mailed Oct. 6, 2014", 7 pgs.
"U.S. Appl. No. 12/484,778, Advisory Action mailed Apr. 2, 2015", 3 pgs.
"U.S. Appl. No. 12/484,778, Final Office Action mailed Jan. 26, 2015", 9 pgs.
"U.S. Appl. No. 12/484,778, Non Final Office Action mailed Aug. 26, 2014", 7 pgs.
"U.S. Appl. No. 12/484,778, Response filed Mar. 24, 2015 to Final Office Action mailed Jan. 26, 2015", 9 pgs.
"U.S. Appl. No. 12/484,811, Non Final Office Action mailed Aug. 14, 2014", 7 pgs.
"U.S. Appl. No. 12/694,328, Final Office Action mailed Oct. 6, 2014", 15 pgs.
"European Search Report for EP Application No. 06824992.9 mailed Aug. 10, 2011", 5 pgs.

(56) References Cited

OTHER PUBLICATIONS

"Examiner's First Report on AU2011202667 mailed May 17, 2012".
"Pericardial Heart Valves, Edwards Lifesciences, Cardiovascular Surgery FAQ", [Online]. Retrieved from the Internet: <URL: http://www.edwards.com/products/cardiovascularsurgeryfaq.htm., (Accessed on Nov. 14, 2010), 1 pg.
"Southern Lights Biomaterials Homepage", [Online]. Retrieved from the Internet: <URL:, (Accessed Jan. 7, 2011), 3 pgs.
"Supplemental Search Report from EP Application No. 04813777.2 mailed Aug. 19, 2011", 2 pgs.
"Supplemental Search Report from EP Application No. 05758878.2 mailed Oct. 24, 2011", 2 pgs.
"Supplemental Search Report, EP Application No. 04815634.3 mailed Aug. 19, 2011", 2 pgs.
Andersen, H. R., et al., "Transluminal implantation of artificial heart valves. Description of a new expandable aortic valve and initial results with implantation by catheter technique in closed chest pigs", Euro. Heart J. 13, (May 1992), 704-708.
Atwood, A., et al., "Insertion of Heart Valves by Catheterization", The Capstone Design Course Report. MIME 1501-1502. Technical Design Report. Northeastern University., (Nov. 5, 2007), 1-93.
Atwood, A., et al., "Insertion of Heart Valves by Catheterization", Project Supervised by Prof. S. Muftu of Northeaster University 2001-2002: 36-40, (May 2002) 4 pgs.
Bodnar. E., et al., "Chapter 13—"Extinct" Cardiac Valve Prostheses", In: Replacement Cardiac Valves, Pergamon Publishing Corporation. New York, (1991), 307-332.
Boudjemline, Y., et al., "Percutaneous implantation of a biological valve in the aorta to treat aortic valve insufficiency—a sheep study", Med Sci. Monit, vol. 8, No. 4, (2002), BR113-BR116.
Boudjemline, Y., et al., "Percutaneous implantation of a valve in the descending aorta in lambs", Euro. Heart J., 23, (Jul. 2002), 1045-1049.
Boudjemline, Y., et al., "Percutaneous pulmonary valve replacement in a large right ventricular outflow tract: an experimental study". Journal of the Americal College of Cardiology; 43(6), (Mar. 2004), 1082-7087.
Boudjemline, Y., et al., "Percutaneous valve insertion: A new approach?", J. of Thoracic and Cardio. Surg., 125(3), (Mar. 2003), 741-743.
Boudjemline, Y. et al., "Steps Toward Percutaneous Aortic Valve Replacement", Circulation.,105, (Feb. 2002), 775-778.
Cribier, A., et al., "Early Experience with Percutaneous Transcatheter Implantation of Heart Valve Prosthesis for the Treatment of End-Stage Inoperable Patients with Calcific Aortic Stenosis", J. of Am. Coll. Of Cardio., 43(4), (Feb. 2004), 698-703.
Cribier, A., et al., "Percutaneous Transcatheter Implantation of an Aortic Valve Prothesis for Calcific Aortic Stenosis: First Human Case", Percutaneous Valve Technologies, Inc., TCT 2002, (Nov. 2002), 16 pgs.
Cribier, A., et al., "Percutaneous Transcatheter Implantation of an Aortic Valve Prosthesis for Calcific Aortic Stenosis: First Human Case Description.", Circulation, 106, (Dec. 2002), 3006-3008.
Cunliffe, H. R., et al., "Glutaraldehyde Inactivation of Exotic Animal Viruses in Swine Heart Tissue", Applied and Environmental Microbiology; vol. 37, No. 5., (May 1979), 1044-1046.
Ferrari, M., et al., "Percutaneous transvascular aortic valve replacement with self expanding stent-valve device.", Poster from the presentation given at SMIT 2000, 12th.International Conference, (Sep. 5, 2000), 1 pg.
Haug, et al., ""Everting Heart Valve"", U.S. Appl. No. 12/492,512, filed Jun. 26, 2009.
Haug, et al., ""Methods and apparatus for endovascularly replacing a heart valve"", U.S. Appl. No. 11/716,123, filed Mar. 9, 2007.
Haug, et al., ""Methods and apparatus for endovascularly replacing a patient's heart valve"", U.S. Appl. No. 12/028,452, filed Feb. 8, 2008.
Hijazi, Z. M., "Transcatheter Valve Replacement: A New Era of Percutaneous Cardiac Intervention Begins", J. of Am. College of Cardio. 2004; 43(6), (Mar. 2004), 1088-1089.

Hourihan, Maribeth, et al., "Transcatheter Umbrella Closure of Valvular and Paravalvular Leaks", JACC, vol. 20, No. 6, , (Nov. 15, 1992), 1371-1377.
Huber, C. H., et al., "Do valved stents compromise coronary flow?", European Journal of Cardio-thoracic Surgery. 2004; vol. 25, (May 2004), 754-759.
Knudsen, L. L., et al., "Catheter-implanted prosthetic heart valves", Int'l J. of Art. Organs; 1993; 16(5), (May 1993), 253-262.
Kort, S., et al., "Minimally invasive aortic valve replacement: Echocardiographic and clinical results.", Am. Heart J. 2001; 142(3), (Sep. 2001), 476-481.
Levy, Charles, et al., "Mycobacterium Chelonei Infection of Porcine Heart Valves", vol. 297, No. 12, The New England Journal of Medicine, (Sep. 2001), 667-668.
Love, C., et al., "", Journal of Cardiac Surgery. 1991; 6(4), (Dec. 1991), 499-507.
Lutter, G., et al., "Percutaneous aortic valve replacement: An experimental study. I. Studies on implantation", J. of Thoracic and Cardio. Surg. 2002; 123(4), (Apr. 2002), 768-776.
Moulopoulos, S. D., et al., "Catheter-Mounted Aortic Valves", Annals of Thoracic Surg. 1971; 11(5), (May 1971), 423-430.
Paniagua, D., et al., "HeartWatch 2004", Texas Heart Institute Spring 2004 Edition, (2004), 1-8.
Paniagua, D., et al., "Percutaneous heart valve in the chronic in vitro testing model.", Circulation. 2002; 106, (Sep. 2002), E51-E52.
Paul, et al., ""Medical Devices and Delivery Systems for Delivering Medical Devices"", U.S. Appl. No. 12/578,447, filed Oct. 13, 2009.
Pavcnik, D., et al., "Percutaneous bioprosthetic veno valve: A longterm study in sheep.", J. of Vascular Surg. 2002; 35(3), (Mar. 2002), 598-603.
Phillips, S. J., et al., Phillips, S. J. et al. "A Temporary Catheter-Tip Aortic Valve: Hemodynamic Effects on Experimental Acute Aortic Insufficiency", Annals of Thoracic Surg. 1976; 21(2), (Feb. 1976), 134-136.
Salahieh, et al., ""Repositionable heart valve and method"", U.S. Appl. No. 12/264,082, filed Nov. 3, 2008.
Salahieh, et al., ""Everting heart valve"", U.S. Appl. No. 12/269,213, filed Nov. 12, 2008.
Salahieh, et al., ""Externally expandable heart valve anchor and method"", U.S. Appl. No. 11/531,980, filed Sep. 14, 2006.
Salahieh, et al. ""Low profile heart valve and delivery system"", U.S. Appl. No. 12/132,304, filed Jun. 3, 2008.
Salahieh, et al. ""Medical Device Delivery"", U.S. Appl. No. 11/314,183, filed Dec. 20, 2005.
Salahieh, et al., ""Medical implant deployment tool"", U.S. Appl. No. 11/274,889, filed Nov. 14, 2005.
Salahieh, et al., ""Methods and apparatus for endovascularly replacing heart valve"", U.S. Appl. No. 11/532,019, filed Sep. 14, 2006.
Salahieh, et al., ""Methods and Apparatus for Performing Valvuloplasty"", U.S. Appl. No. 11/314,969, filed Dec. 20, 2005.
Salahieh, et al., ""Systems and Methods for Delivering a Medical Implant"", U.S. Appl. 11/706,549, filed Feb. 14, 2007.
Salahieh, et al., ""Two-Part Package for Medical Implant"", U.S. Appl. No. 11/275,913, filed Feb. 2, 2006.
Sochman, J., et al., "Percutaneous Transcatheter Aortic Disc Valve Prosthesis Implantation: A Feasibility Study", Cardiovasc. Intervent. Radiol. 2000; 23, 384-388, (Oct. 2000).
Stuart, M., "In Heart Valves, a Brave, New Non-Surgical World", Start Up, (Feb. 2004), 9-17.
Vahanian, A., et al., "Percutaneous Approaches to Valvular Disease", Circulation. 2004; 109, (Apr. 2004), 1572-1579.
Van Herwerden, L. A., et al., "Percutaneous valve implantation: back to the future?", Euro. Heart J. 2002; 23(18), (Sep. 2002), 1415-1416.
Zhou, J. Q., et al., "Self-expandable valved stent of large size: offbypass implantation in pulmonary position", Eur. J. Cardiothorac.; 24, (Aug. 2003), 212-216.
Agatielio, C., et al., "Balloon aortic valvuoplasty in the adult. Immediate results and in-hospital complications in the latest series of 141 consecutive patients at the University Hospital of Rouen (2002-2005)", Arch Mal Couer Veiss, 99 (3), (Mar. 2006), 2 pgs.

(56) References Cited

OTHER PUBLICATIONS

Bauer, Fabrice, et al., "Acute Improvement in Global and Regional Left Ventricular Systolic Function After Percutaneous Heart Valve Implantation in Patients With Symptomatic Aortic Stenosis", Circulation, (Sep. 14, 2004), 1473-1476.

Bronzwaer, Jean G.F., et al., "Comparative Effects of Pacing-Induced and Balloon Coronary Occlusion Ischemia on Left Ventricular Diastolic Function in Man", Circulation, vol. 84, No. 1, (Jul. 1991), 211-222.

Daehnert, I., "Rapid right ventricular pacing is an alternative to adenosine in catheter interventional procedures for congenital heart disease", Heart 90, (2004), 1047-1050.

Ing, Frank F., et al., "Transcatheter Aortic Valvuoplasty Assisted by Right Ventricular Pacing", J Am Coll Cardiol, (Mar. 6, 2002), 1190-1196.

Lichtenstein, Samuel V., et al., "Transapical Transcatheter Aortic Valve Implantation in Humans—Initial Clinical Experience", Circulation, (Aug. 8, 2006), 591-596.

Mehta, C., "How to achieve balloon stability in aortic valvuloplasty using rapid ventricular pacing", Images in Paediatric Cardiology 6 (4), (Dec. 2004), 31-37.

Waither, Thomas, et al., "Transapical approach for sutureless stent-fixed aortic valve implantation: experimental results", European Journal of Cardio-thoracic Surgery, 29, (2006), 703-708.

Walther, Thomas, et al., "Minimally Invasive transapical beating heart aortic valve implantation—proof of concept", European Journal of Cardio-thoracic Surgery, 31, (2007), 9-15.

Webb, John G., et al., "Rapid Pacing to Facilitate Transcatheter Prosthetic Heart Valve Implantation", Catheterization and Cardiovascular Interventions, 66, (2006), 199-204.

U.S. Appl. No. 12/484,769, Appeal Decision mailed Jan. 29, 2016, 7 pgs.

U.S. Appl. No. 14/925,618, Preliminary Amendment filed Dec. 14, 2015, 6 pgs.

\* cited by examiner

METHOD AND APPARATUS FOR PACING DURING REVASCULARIZATION

CLAIM OF PRIORITY

This application is a continuation of and claims the benefit of priority under 35 U.S.C. §120 to U.S. patent application Ser. No. 13/113,706, filed on May 23, 2011, now issued as U.S. Pat. No. 8,452,400, which is a continuation of and claims the benefit of priority under 35 U.S.C. §120 to U.S. patent application Ser. No. 11/113,828, filed on Apr. 25, 2005, now issued as U.S. Pat. No. 7,962,208, which is hereby incorporated by reference herein in its entirety.

TECHNICAL FIELD

This document relates generally to cardiac pacing systems and particularly to a system for delivering pacing pulses during a revascularization procedure.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

When a blood vessel such as the coronary artery is partially or completely occluded, a revascularization procedure such as percutaneous transluminal coronary angioplasty (PCTA) can be performed to reopen the occluded blood vessel. However, the revascularization procedure itself involves a temporary occlusion of the coronary artery. In addition, plaques dislodged and displaced by the revascularization procedure may enter small blood vessels branching from the blood vessel in which the revascularization is performed, causing occlusion of these small blood vessels. This complication is referred to as "snow plow effect." The revascularization procedure may also cause distal embolization, i.e., obstruction of the artery caused by the plaque dislodged during the procedure. The temporary occlusion, snow plow effect, and distal embolization may each cause cardiac injuries such as further expansion of the region of infarcted tissue. In addition, the revascularization procedure is known to increase the risk for occurrences of arrhythmia.

Therefore, there is a need for minimizing cardiac injury and preventing arrhythmias during the revascularization procedure.

SUMMARY

A system for use during revascularization includes a catheter having an adjustable balloon for delivery a stent and a pacemaker to deliver one or more pacing pulses to a patient's heart to prevent or reduce cardiac injury associated with the revascularization procedure. In one embodiment, a system includes a catheter, one or more pacing electrodes, and a pacemaker. The catheter includes a proximal end portion, a distal end portion, and an elongate body extending therebetween. The distal end portion includes an adjustable balloon for delivering a stent. The one or more pacing electrodes configured to deliver one or more pacing pulses to a heart of a patient. The pacemaker is configured to generate the one or more pacing pulses to be delivered to the heart via the one or more pacing electrodes. The one or more pacing pulses are delivered at a rate substantially higher than the patient's intrinsic heart rate without being synchronized to the patient's intrinsic cardiac contractions, and are delivered before, during, or after an ischemic event to prevent or reduce cardiac injury.

In one embodiment, a method for delivering cardiac pacing to a patient is provided. A stent is delivered using a catheter including a stent delivery system causing an ischemic event in a patient. The heart of the patient is paced before, during, or after the ischemic event in a manner such that the pacing pulses are delivered at a rate substantially higher than the patient's intrinsic heart rate without being synchronized to the patient's intrinsic cardiac contractions.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a pacing system for minimizing damage to the myocardial tissue and preventing arrhythmias during a revascularization procedure that requires temporary occlusion of one or more blood vessels. In a specific application, this system provides for cardiac protection pacing during a percutaneous transluminal coronary angioplasty (PTCA) procedure. Cardiac protection pacing includes the delivery of a pacing therapy before, during, and/or after the temporary occlusion of a coronary artery associated with the PTCA procedure, for preventing or reducing adverse effects of the occlusion, which is an ischemic event. The pacing therapy can be delivered at almost any time during a revascularization procedure, as soon as pacing electrodes are in place, without substantially interfering with the revascularization procedure.

To deliver pacing pulses during a revascularization procedure, one or more pacing electrodes are incorporated onto the distal end portion of a PTVI device. Examples of such PTVI device include guide wires, dilatation balloon catheters, stent delivery systems, brachytherapy devices, atherectomy devices, distal embolization protection devices, and guiding catheters. A pacemaker is connected to the proximal end portion of the PTVI device to deliver the pacing pulses to the heart through the one or more electrodes. In one embodiment, the pacemaker is an external pacing device such as a pacing system analyzer. This approach to cardiac protection pacing allows delivery of pacing pulses as soon as the PTVI device is inserted.

Figure 1:
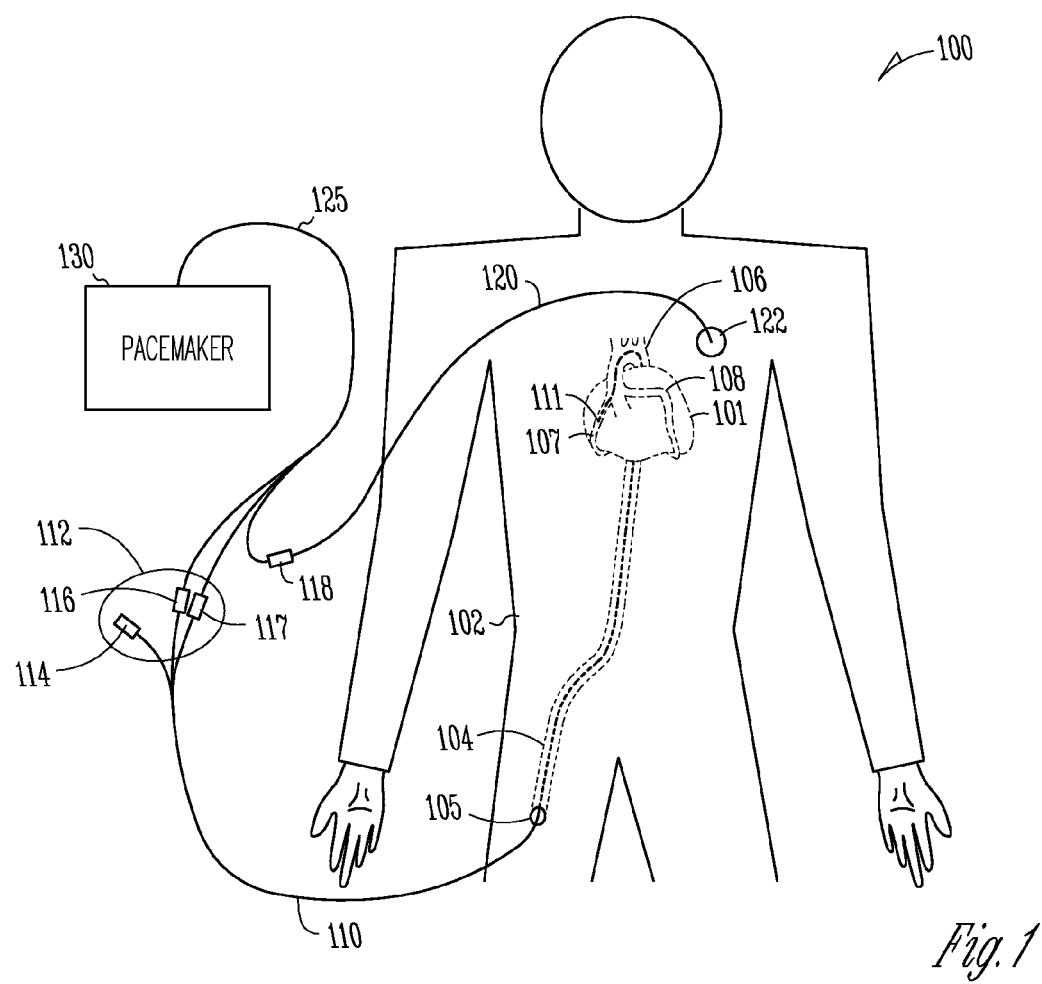
FIG. 1 is an illustration of an embodiment of a system providing for pacing during revascularization and portions of an environment in which the system is used.

FIG. 1 is an illustration of an embodiment of a system 100 providing for pacing during revascularization and portions of an environment in which system 100 is used. System 100 includes a PTVI device 110, a pacemaker 130, and a cable 125 connecting PTVI device 110 and pacemaker 130. When needed, system 100 also includes a reference electrode 122, which is a surface electrode, such as a skin patch electrode, connected to a lead 120. Lead 120 is connected to a connector 118 allowing its connection to cable 125.

PTVI device 110 is used during a revascularization procedure and includes a distal end portion 111 for intravascular placement and a proximal end portion 112. Proximal end portion 112 includes a proximal end device 114 and pacing connectors 116 and 117. Proximal end device 114 includes various connectors and other structures allowing manipulation of PTVI device 110 including the percutaneous transluminal insertion of the device and operation of an angioplasty device at distal end 111. Pacing connectors 116 and 117 provide for electrical connections between cable 125 and PTVI device 110. In one embodiment, as illustrated in FIG. 1, PTVI device 110 is a percutaneous transluminal coronary angioplasty (PTCA) device used in a PTCA procedure. During the PTCA procedure, an opening 105 is made on a femoral artery 104 in a patient's body 102. PTVI device 110 is inserted into femoral artery 104 and advanced to an aorta 106 and then to a right coronary artery 107, which is narrowed or blocked. The angioplasty device at distal end 111 is then used to open up the blocked right coronary artery 107. In another embodiment, PTVI device 110 is used to open up a blocked left coronary artery 108.

Distal end portion 111 of PTVI device 110 includes one or more pacing electrodes to allow pacing pulses to be delivered to a heart 101 during the PTCA procedure. In one embodiment, pacing pulses are delivered through two pacing electrodes on distal end portion 111 of PTVI device 110. In another embodiment, pacing pulses are delivered through a pacing electrode on distal end portion 111 of PTVI device 110 and surface electrode 122 functioning as the return electrode for pacing.

Pacemaker 130 delivers pacing pulses by following a cardiac protection pacing sequence. In one embodiment, the cardiac protection pacing sequence provides for cardiac protection pacing following an ischemic event to prevent arrhythmias and cardiac injuries caused by the ischemic event. In one embodiment, pacemaker 130 is an external pacemaker such as a pacing system analyzer (PSA). In another embodiment, pacemaker 130 includes an implantable pacemaker adapted for external use.

It is to be understood that FIG. 1 is for illustrative, but not restrictive, purposes. For example, the physical structure of proximal end portion 112 depends on functional and ease-of-use considerations. Proximal end device 114 represents a structure that accommodates all the mechanical connection and access requirements, which depend on the specific configuration and function of PTVI device 110. In one embodiment, proximal end device 114 includes an integrated device as illustrated in FIG. 1. In another embodiment, proximal end device 114 branches out into multiple connectors and/or other devices. Pacing connectors 116 and 117 represent a structure that accommodates all the electrical connections required for delivering pacing pulses from pacemaker 130 to PTVI device 110. The number of pacing connectors depends on the number of pacing electrodes incorporated onto PTVI device 110 and how it is to be connected to cable 125. In one embodiment, when more than one electrical connection is incorporated onto PTVI device 110, proximal end portion 112 includes branched-out pacing connectors such as pacing connectors 116 and 117 as illustrated in FIG. 1. In another embodiment, proximal end portion 112 includes a single connector providing for multiple, independent electrical connections.

Figure 2:
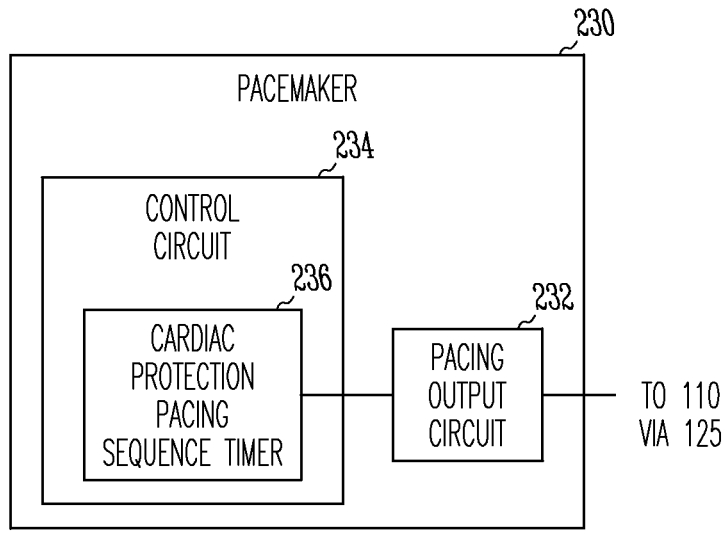
FIG. 2 is an illustration of an embodiment of a pacemaker providing for pacing during revascularization.

FIG. 2 is an illustration of an embodiment of a pacemaker 230 that provides for pacing during revascularization. Pacemaker 230 is a specific embodiment of pacemaker 130 and includes a pacing output circuit 232 and a control circuit 234. In one embodiment, pacemaker 230 further includes a user interface to allow a user to control the delivery of the pacing pulses by controlling the pacing parameters and/or the timing of the delivery.

Pacing output circuit 232 delivers pacing pulses to PTVI device 110 through cable 125. Control circuit 234 controls the delivery of the pacing pulses. In one embodiment, as illustrated in FIG. 2, control circuit 234 includes a cardiac protection pacing sequence timer 236, which times a predetermined cardiac protection pacing sequence. The cardiac protection pacing sequence is predetermined to provide cardiac protection pacing before, during, and/or after an ischemic event such as the occlusion of a coronary artery by PTVI device 110 during a PTCA procedure.

Figure 3:
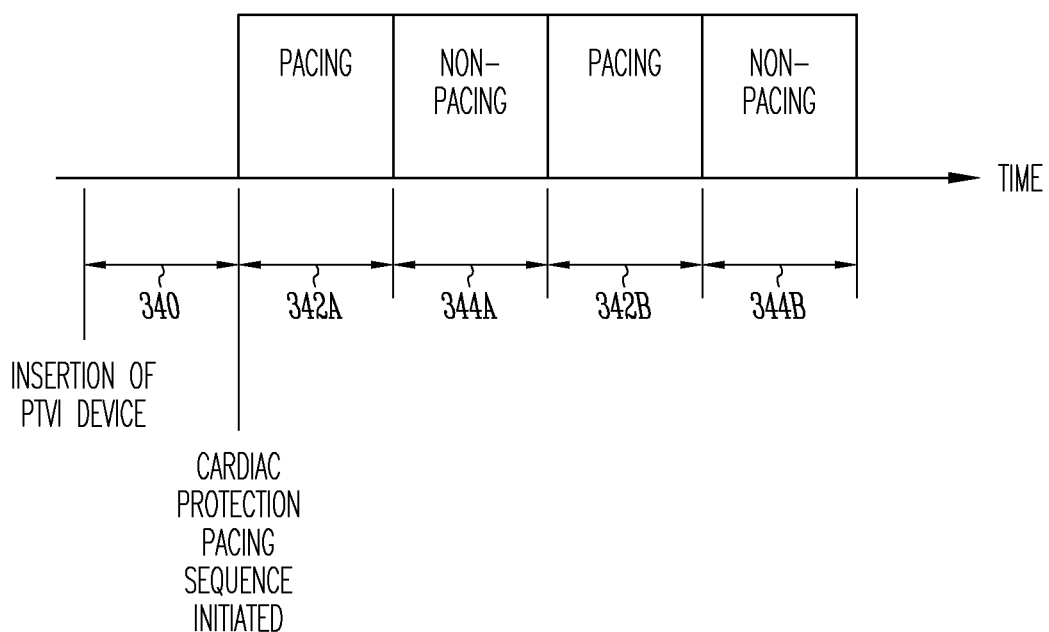
FIG. 3 is a timing diagram illustrating an exemplary embodiment of a cardiac protection pacing sequence for the pacing during revascularization.

FIG. 3 is a timing diagram illustrating an exemplary embodiment of a cardiac protection pacing sequence for pacing during a revascularization procedure such as a PTCA procedure. The cardiac protection pacing sequence is initiated after a time interval 340, which starts when the insertion of PTVI device into body 102 is completed. Time interval 340 expires before, during, and/or after an ischemic event that occurs when the blood vessel at the revascularization site is substantially occluded by PTVI device 110. In one embodiment, the cardiac protection pacing sequence is applied repeatedly, before, during, and/or after the ischemic event, during the revascularization procedure.

In the embodiment illustrated in FIG. 3, the cardiac protection pacing sequence includes alternating pacing and non-pacing periods. Each pacing period is a pacing duration during which the pacing pulses are delivered in a predetermined pacing mode. The non-pacing period is a non-pacing duration during which no pacing pulses is delivered. In one embodiment, during each pacing period, rapid, asynchronous pacing is applied. In other words, pacing pulses are delivered at a rate substantially higher than the patient's intrinsic heart rate without being synchronized to the patient's intrinsic cardiac contractions. For illustrative purpose only, FIG. 3 shows a cardiac protection pacing sequence that includes two cycles of alternating pacing and non-pacing periods: pacing period 342A, non-pacing periods 344A, pacing period 342B, and non-pacing periods 344B. In one embodiment, the number of the cycles of alternating pacing and non-pacing periods is programmable, and each of the pacing and non-pacing periods is programmable. In one embodiment, the cardiac protection pacing sequence is initiated before the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardiac protection pacing sequence initiated before the ischemic event includes 3 cycles of alternating pacing and non-pacing periods each being approximately 5-minute long. In one embodiment, the cardiac protection pacing sequence is initiated during the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardiac protection pacing sequence delivered during the ischemic event includes 3 cycles of alternating pacing and non-pacing periods each being approximately 5-minute long. In one embodiment, the cardiac protection pacing sequence is initiated after the ischemic event and includes approximately 1 to 4 cycles of alternating pacing and non-pacing periods. The pacing period is in a range of approximately 10 seconds to one minute. The non-pacing period is in a range of approximately 10 seconds to one minute. In one specific example, the cardiac protection pacing sequence delivered after the ischemic event includes 2 to 4 cycles of alternating pacing and non-pacing periods each being approximately 30-second long.

In various other embodiments, the cardiac protection pacing sequence includes pacing at one or more atrial tracking or other pacing modes. Examples of pacing modes used in such a cardiac protection pacing sequence include VDD, VVI, and DDD modes. In various embodiments, the VVI and DDD modes are delivered with a lower rate limit higher than the patient's intrinsic heart rate. In one embodiment, pacing therapy is delivered to prevent restenosis. In another embodiment, pacing therapy is delivered to treat an arrhythmia during the revascularization procedure, for example, when the patient experiences bradycardia during the procedure.

In one embodiment, the pacing pulses are delivered according to the cardiac protection pacing sequence through PTVI device 110 during the revascularization procedure. After the revascularization procedure, if an implantable pacemaker is implanted into the patient, pacing therapy is delivered to heart 101 through one or more implantable leads from the implantable pacemaker. The pacing therapy includes delivering pacing pulses according to a pacing sequence that is substantially identical or similar to the cardiac protection pacing sequence applied during the revascularization procedure. The pacing sequence is delivered according to a predetermined schedule, such as on a predetermined periodic basis. This prevents or reduces possible cardiac injury after the revascularization, including cardiac injury and occurrences of arrhythmia caused by ischemic events including myocardial infarction that may be experienced by the patient after the implantation of the implantable pacemaker.

Figure 4:
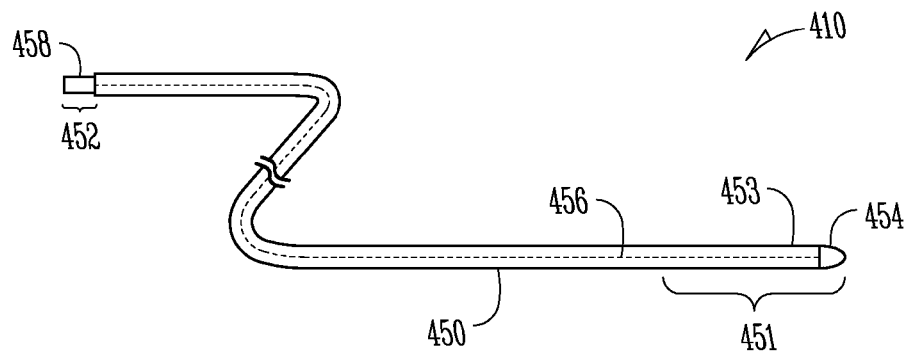
FIG. 4 is an illustration of an embodiment of a PTVI device with pacing electrodes.

FIG. 4 is an illustration of an embodiment of a PTVI device 410. PTVI device 410 is a specific embodiment of PTVI device 110 and has an elongate body 450 between a distal end portion 451 and a proximal end portion 452. Distal end portion 451 is configured for intravascular placement and includes a distal tip 453. Distal tip 453 includes a pacing electrode 454. A conductor 456 extends longitudinally within elongate body 450 and connected between pacing electrode 454 and a connector 458, which is part of proximal end portion 452.

In one embodiment, elongate body 450 is an elongate cylindrical shaft having a diameter in a range of approximately 0.2 mm to 1.5 mm, and PTVI device 410 has a length in a range of approximately 30 cm to 300 cm. In another embodiment, elongate body 450 is an elongate tubular body having an outer diameter in a range of approximately 0.5 mm to 8 mm and an inner diameter (of a lumen) in a range of approximately 0.4 mm to 7 mm. In one embodiment, PTVI device 410 is a guide wire such as a coronary guide wire. PTVI device 410 is formed by conductor 456, which is insulated throughout its length except for pacing electrode 454 and connector 458. As the core of the guide wire, conductor 456 is made of a metallic material such as stainless steel, alloys of nickel, titanium, and cobalt, and is insulated with a material such as silicone, polyurethane, Teflon, and polytetrafluoroethylene (PTFE). Electrode 454 is made of a metallic material such as platinum, and iridium alloy. In another embodiment, conductor 456 is a metal wire other than the core of the guide wire. In another embodiment, PTVI device 410 is a guiding catheter such as a coronary guiding catheter. The coronary guiding catheter includes an elongate tubular body with a lumen extending between distal end portion 452 and proximal end portion 452. In another embodiment, PTVI device 410 includes two or more electrodes in distal end portion 451 and two or more conductors each connected between one of the electrodes and connector 458, which is a multi-conductor connector allowing for two or more electrically insulated connections.

Figure 5:
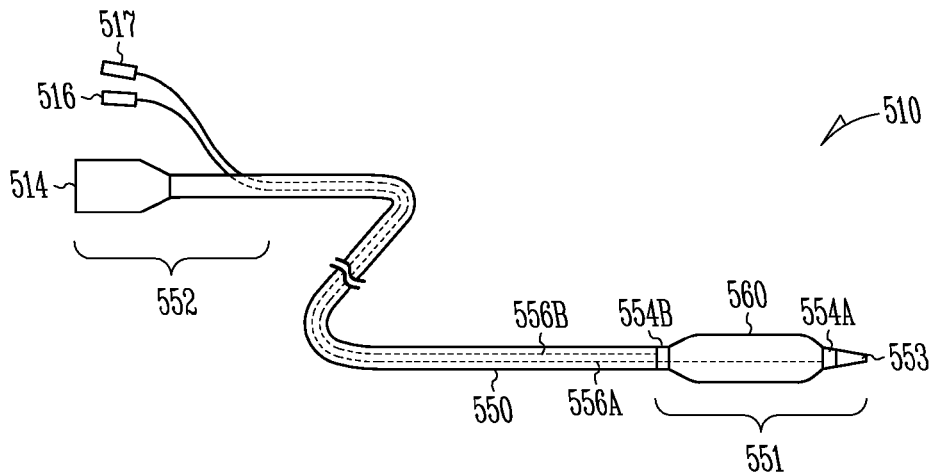
FIG. 5 is an illustration of another embodiment of a PTVI device with pacing electrodes.

FIG. 5 is an illustration of another embodiment of a PTVI device 510. PTVI device 510 is another specific embodiment of PTVI device 110 and has an elongate body 550 between a distal end portion 551 and a proximal end portion 552. Distal end portion 551 is configured for intravascular placement and includes a distal tip 553 and an angioplasty device 560. Angioplasty device 560 has one end approximately adjacent to distal tip 553 and another end coupled to elongate body 550. In various embodiments, angioplasty device 560 allows for application of an angioplasty therapy such as vascular dilatation, stent delivery, brachytherapy (radiotherapy), atherectomy, or embolic protection. In one embodiment, angioplasty device 560 includes an adjustable portion that has controllable expandability and contractibility. In one specific embodiment, angioplasty device 560 includes a balloon that is inflated and deflated through a passageway longitudinally extending within elongate body 550 and connected between the chamber of the balloon and a connector at proximal end portion 552. The balloon is inflatable using an air pump connected to that connector. In one embodiment, distal tip 553 is a tapered tip that facilitates the insertion of PTVI device 510 into a blood vessel. A pacing electrode 554A is approximately adjacent to one end of angioplasty device 560. Another pacing electrode 554B is approximately adjacent to the other end of angioplasty device 560. A conductor 556A extends longitudinally within elongate body 550 and is connected between pacing electrode 554A and a pacing connector 516, which is part of proximal end portion 552. A conductor 556B extends longitudinally within elongate body 550 and is connected between pacing electrode 554B and a pacing connector 517, which is also part of proximal end portion 552. In an alternative embodiment, pacing connectors 516 and 517 are physically integrated into one multi-conductor connector. Proximal end portion 552 also includes a proximal end device 514. Proximal end device 514 represents a structure that accommodates all the mechanical connection and access requirements, which depend on the function of angioplasty device 560. In one embodiment, proximal end device 514 includes an integrated device as illustrated in FIG. 5. In another embodiment, proximal end device 514 branches out into multiple connectors and/or other devices.

In one embodiment, elongate body 550 is an elongate cylindrical shaft having a diameter in a range of approximately 1 mm to 5 mm. PTVI device 510 has a length in a range of approximately 50 cm to 150 cm. In one embodiment, angioplasty device 560 has a fixed, substantially cylindrical shape with a diameter in a range of approximately 1 mm to 10 mm. In another embodiment, angioplasty device 560 has an adjustable, substantially cylindrical or semi-spherical shape with a maximum diameter in a range of approximately 1 mm to 10 mm when fully expanded and a maximum diameter in a range of approximately 0.5 mm to 5 mm when fully contracted. In one embodiment, PTVI device 510 is a PTCA catheter and includes a lumen longitudinally extending within elongate body 550 to accommodate at least a portion of a guide wire such as PTVI device 410. In one embodiment, conductors 556A and 556B are each made of a metallic material such as stainless steel and alloys of nickel, titanium, and cobalt. Electrodes 554A and 554B are each made of a metallic material such as platinum, and iridium alloy. Elongate body 550 has a tubular outer shell made of a material such as silicone, polyurethane, Teflon, and polytetrafluoroethylene (PTFE).

In one alternative embodiment, PTVI device 510 includes one electrode in distal end portion 551 and one conductor connected between that electrode and a pacing connector in proximal end portion 552. In another alternative embodiment, PTVI device 510 includes three or more electrodes in distal end portion 551 and three or more conductors each connected between one of the electrodes a pacing connector in proximal end portion 552.

Figure 6:
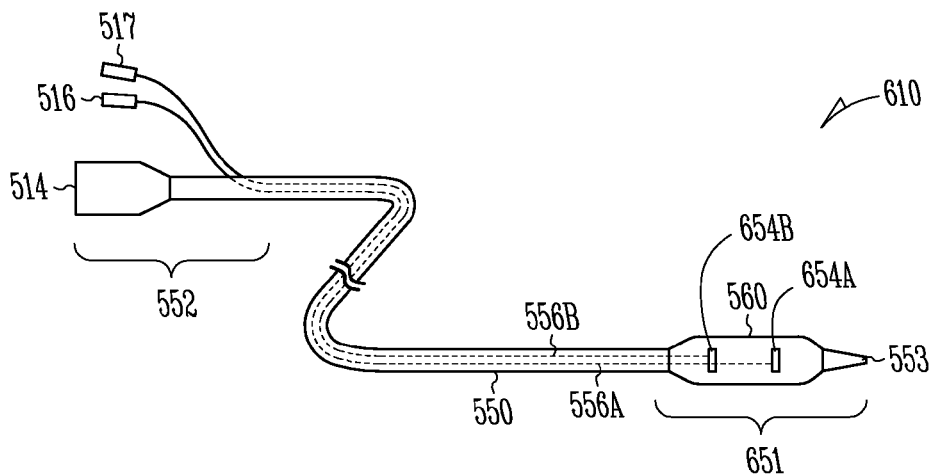
FIG. 6 is an illustration of another embodiment of a PTVI device with pacing electrodes.

FIG. 6 is an illustration of another embodiment of a PTVI device 610 with pacing electrodes. PTVI device 610 is another specific embodiment of PTVI device 110 and is similar to PTVI device 510 except for the location of the pacing electrodes. PTVI device 610 has a distal end portion 651, where pacing electrodes 654A and 654B are attached onto angioplasty device 560. In one specific embodiment, pacing electrodes 654A and 654B are each approximately adjacent to one end of angioplasty device 560.

PTVI devices 410, 510, and 610 are illustrated in FIGS. 4-6 for illustrative but not restrictive purposes. For example, the one or more pacing electrodes can be distributed on the distal portion of a PTVI device in any way allowing proper delivery of pacing pulses. In various embodiments, the one or more pacing electrodes can be distributed on the angioplasty device, the distal tip, and/or the elongate body at the distal end portion of the PTVI device.

FIGS. 7-13 illustrate exemplary specific embodiments of the distal end of a PTVI device with one or more pacing electrodes. In one embodiment, PTVI device 410, 510, and 610 are each made by modifying a selected product of Guidant Corporation's Vascular Intervention division ("Guidant VI," Temecula, Calif.) to include one or more pacing electrodes. Examples of such a selected product are illustrated in FIGS. 7-13. According to the present subject matter, one or more pacing electrodes are incorporated onto any PTVI device as deemed appropriate by one skilled in the art. Such PTVI devices include, but are not limited to, devices that belong to the same category as those illustrated in FIGS. 7-13.

Figure 7:
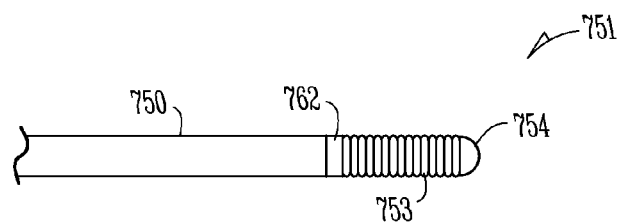
FIG. 7 is an illustration of an exemplary specific embodiment of the distal end portion of a PTVI device with pacing electrode(s).

FIG. 7 is an illustration of an embodiment of the distal end portion 751, which is an exemplary specific embodiment of distal end portion 451. Distal end portion 751 is the distal portion of a coronary guide wire (Guidant VI's HI-TORQUE PILOT™ 50 Guide Wire with Hydrocoat hydrophilic coating) modified to include a pacing electrode 754. The coronary guide wire includes an elongate body 750 being an insulated conductive wire that extends to a distal tip 753. The coronary guide wire has a length of approximately 190 cm or 300 cm, depending on the specific product model, and a diameter of approximately 0.014 inches (0.3556 mm). The conductive wire is connected to pacing electrode 754 at the distal end of distal tip 753. Distal end portion 751 also includes a radiopaque marker 762, which allows for measurement of lesion length. In one embodiment, the single-electrode configuration allows the coronary guide wire to have a relatively small diameter. In one embodiment, pacing pulses are delivered using a unipolar electrode configuration, with a return electrode such as reference electrode 122.

Figure 8:
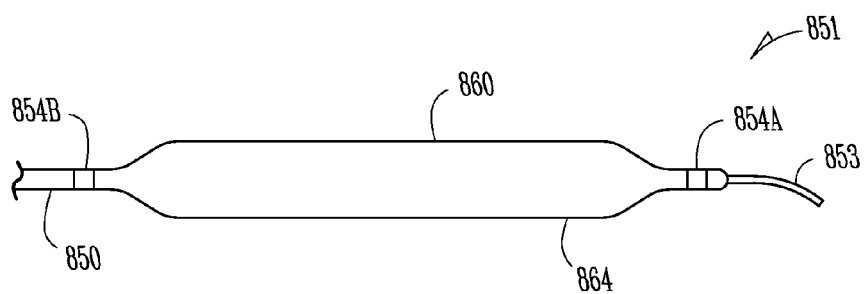
FIG. 8 is an illustration of another exemplary specific embodiment of the distal end portion of a PTVI device with pacing electrode(s).

FIG. 8 is an illustration of an embodiment of the distal end portion 851, which is an exemplary specific embodiment of distal end portion 551. Distal end portion 851 is the distal portion of a coronary dilatation balloon catheter (Guidant VI's VOYAGER™ RX Coronary Dilatation Catheter) modified to include pacing electrodes 854A and 854B. Distal end portion 851 is extended from an elongate body 850 and includes a tapered tip 853 and an angioplasty device 860. The coronary dilatation balloon catheter has a usable catheter working length of approximately 143 cm and accommodates a guide wire having a maximum diameter of 0.014 inches (0.3556 mm), such as the coronary guide wire illustrated in FIG. 7, that is used for insertion of the catheter. Elongate body 850 includes a shaft having a diameter in a range of approximately 2.0 to 2.8 French, depending on the specific product model. Angioplasty device 860 is a specific embodiment of angioplasty device 560 and includes an adjustable balloon 864 that is approximately adjacent to tapered tip 853. Adjustable balloon 864 is used for coronary dilatation by inflation. When inflated, adjustable balloon 864 has a diameter in a range of 1.5 mm to 4 mm, depending on the specific product model. Pacing electrode 854A is approximately adjacent to one end of adjustable balloon 864. Pacing electrode 854B is approximately adjacent to the other end of adjustable balloon 864. Pacing pulses are delivered using a bipolar configuration with pacing electrodes 854A and 854B, a unipolar configuration using one of pacing electrodes 854A and 854B and a return electrode such as reference electrode 122, or a combination of bipolar and unipolar configurations.

Figure 9:
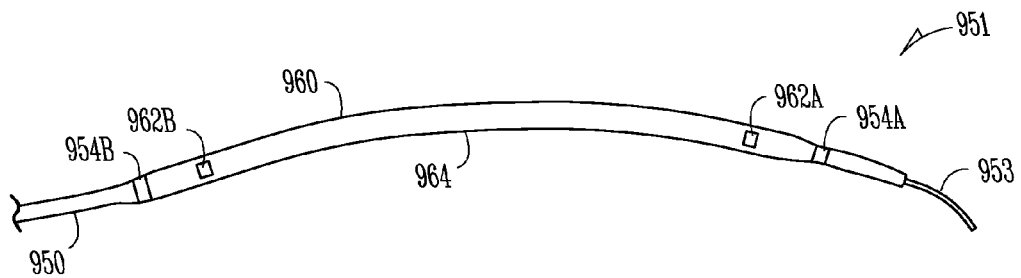
FIG. 9 is an illustration of another exemplary specific embodiment of the distal end portion of a PTVI device with pacing electrode(s).

FIG. 9 is an illustration of an embodiment of the distal end portion 951, which is an exemplary specific embodiment of distal end portion 551. Distal end portion 951 is the distal portion of a stent delivery platform (Guidant VI's GUIDANT MULTI-LINK RX ULTRA™ Coronary Stent System) modified to include pacing electrodes 954A and 954B. Distal end portion 951 is extended from an elongate body 950 and includes a tip 953 and an angioplasty device 960. The stent delivery platform accommodates a guide wire having a maximum diameter of 0.014 inches (0.3556 mm), such as the coronary guide wire illustrated in FIG. 7, that is used for insertion of the device. Angioplasty device 960 is a specific embodiment of angioplasty device 560 and includes an adjustable balloon 964 that is approximately adjacent to tip 953. Adjustable balloon 964 is used for placing a stent in the coronary artery where distal end portion 951 has reached. Depending on the specific product model, the working size of adjustable balloon 964 accommodates stents having a diameter in a range of approximately 3.5 mm to 5 mm and a length in a range of approximately 13 mm to 38 mm. Pacing electrode 954A is approximately adjacent to one end of adjustable balloon 964. Pacing electrode 954B is approximately adjacent to the other end of adjustable balloon 964. Distal end portion 951 also includes a pair of radiopaque markers 962A and 962B on adjustable balloon 964 for indicating the balloon's working length. Pacing pulses are delivered using a bipolar configuration with pacing electrodes 954A and 954B, a unipolar configuration using one of pacing electrodes 954A and 954B and a return electrode such as reference electrode 122, or a combination of bipolar and unipolar configurations.

Figure 10:
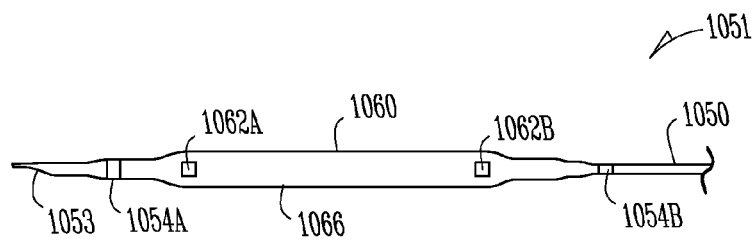
FIG. 10 is an illustration of another exemplary specific embodiment of the distal end portion of a PTVI device with pacing electrode(s).

FIG. 10 is an illustration of an embodiment of the distal end portion 1051, which is an exemplary specific embodiment of distal end portion 551. Distal end portion 1051 is the distal portion of a brachytherapy device (Guidant VI's GALILEO® Intravascular Radiotherapy System) modified to include pacing electrodes 1054A and 1054B. Distal end portion 1051 is extended from an elongate body 1050 and includes a tapered tip 1053 and an angioplasty device 1060. The brachytherapy device accommodates a guide wire having a maximum diameter of 0.014 inches (0.3556 mm), such as the coronary guide wire illustrated in FIG. 7, that is used for insertion of the device. Angioplasty device 1060 is a specific embodiment of angioplasty device 560 and includes an brachytherapy device 1066 that is approximately adjacent to tapered tip 1053 and includes a chamber containing an radiological agent to provide therapeutic doses to the tissue area where distal end portion 1051 has reached. Brachytherapy device 1066 has diameter in a range of approximately 2.5 mm, 3.0 mm, or 3.5 mm and a therapeutic dose length of approximately 32 mm or 52 mm, depending on the specific product model. Pacing electrode 1054A is approximately adjacent to one end of brachytherapy device 1066. Pacing electrode 1054B is approximately adjacent to the other end of brachytherapy device 1066. Distal end portion 1051 also includes a pair of radiopaque markers 1062A and 1062B on brachytherapy device 1066 for indicating the therapeutic dose length. Pacing pulses are delivered using a bipolar configuration with pacing electrodes 1054A and 1054B, a unipolar configuration using one of pacing electrodes 1054A and 1054B and a return electrode such as reference electrode 122, or a combination of bipolar and unipolar configurations.

Figure 11:
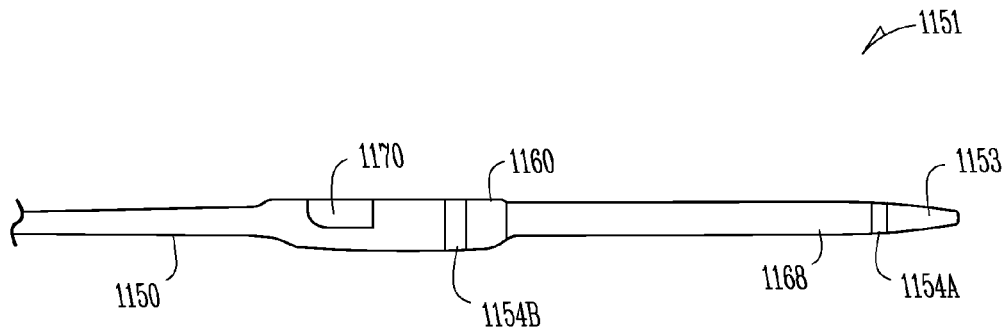
FIG. 11 is an illustration of another exemplary specific embodiment of the distal end portion of a PTVI device with pacing electrode(s).

FIG. 11 is an illustration of an embodiment of the distal end portion 1151, which is an exemplary specific embodiment of distal end portion 551. Distal end portion 1151 is the distal portion of an atherectomy device (Guidant VI's FLEXI-CUT® Directional Debulking System) modified to include pacing electrodes 1154A and 1154B. Distal end portion 1151 is extended from an elongate body 1150 and includes a tapered tip 1153 and an angioplasty device 1160. The atherectomy device has a working length of approximately 134 cm. Angioplasty device 1160, which is a specific embodiment of angioplasty device 560, is an atherectomy device that includes a cylindrical nosecone 1168 that is approximately adjacent to tapered tip 1153 and a cutter 1170 connected to cylindrical nosecone 1168. Cutter 1170 cuts the plaques that block or narrow the portion of the coronary artery where distal end portion 1151 has reached. Cylindrical nosecone 1168 stores the cut plaques. Depending on the specific product model, atherectomy device is capable of operating in blood vessels having diameters ranging from approximately 2.5 mm to 4 mm. Pacing electrode 1154A is on tapered tip 1153 and approximately adjacent to the distal end of cylindrical nosecone 1168. Pacing electrode 1154B is on cutter 1170 and approximately adjacent to the distal end of cutter 1170. Pacing pulses are delivered using a bipolar configuration with pacing electrodes 1154A and 1154B, a unipolar configuration using one of pacing electrodes 1154A and 1154B and a return electrode such as reference electrode 122, or a combination of bipolar and unipolar configurations.

Figure 12:
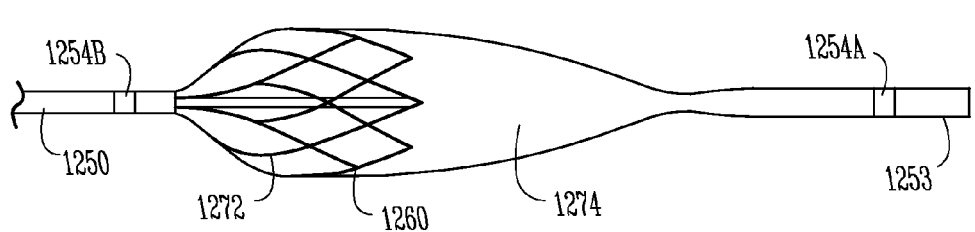
FIG. 12 is an illustration of another exemplary specific embodiment of the distal end portion of a PTVI device with pacing electrode(s).

FIG. 12 is an illustration of an embodiment of the distal end portion 1251, which is an exemplary specific embodiment of distal end portion 551. Distal end portion 751 is the distal portion of a distal embolization protection device (Guidant VI's RX ACCUNET™ Embolic Protection System) modified to include pacing electrodes 1254A and 1254B. Distal end portion 1251 is extended from an elongate body 1250 and includes a tip 1253 and an angioplasty device 1260. Elongate body 1250 is based on a coronary guide wire that has a diameter of 0.014 inches (0.3556 mm) and extends throughout substantially the full length of the distal embolization protection device, which is either 190 cm or 300 cm, depending on the specific product model. Angioplasty device 1260, which is a specific embodiment of angioplasty device 560, is an embolic protection device that includes a filter basket 1272 with a filter membrane 1274 to contain and remove embolic material including plaques dislodged during the angioplasty procedure. Filter basket 1272 is flexible, with available basket diameters (when fully expanded) of 4.5 mm, 5.5 mm, 6.5 mm, and 7.5 mm, depending on the specific product model. Pacing electrode 1254A is on tip 1253. Pacing electrode 1254B is on elongate body 1250 and is approximately adjacent to the proximal end of filter basket 1272. Pacing pulses are delivered using a bipolar configuration with pacing electrodes 1254A and 1254B, a unipolar configuration using one of pacing electrodes 1254A and 1254B and a return electrode such as reference electrode 122, or a combination of bipolar and unipolar configurations.

Figure 13:
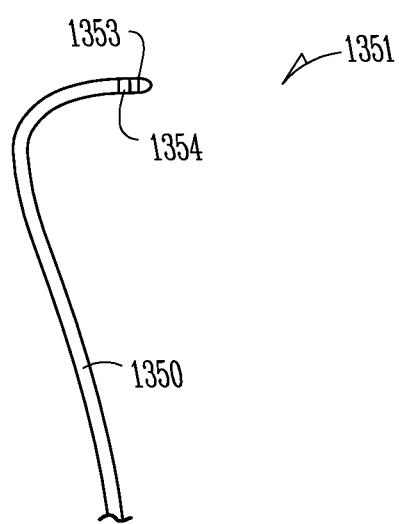
FIG. 13 is an illustration of another exemplary specific embodiment of the distal end portion of a PTVI device with pacing electrode(s).

FIG. 13 is an illustration of an embodiment of the distal end portion 1351, which is another exemplary specific embodiment of distal end portion 451. Distal end portion 1351 is the distal portion of a coronary guiding catheter (Guidant VI's VIKING OPTIMA™ 50 Guiding Catheter) modified to include a pacing electrode 1354. The coronary guiding catheter includes a tubular elongate body 1350 that has a distal tip 1353, and a lumen having a diameter of 6 French (0.068 inches), 7 French (0.078 inches), or 8 French (0.091 inches). In one embodiment, the single-electrode configuration allows the coronary guiding catheter to have a relatively small diameter. In one embodiment, pacing pulses are delivering using a unipolar electrode configuration, with a return electrode such as reference electrode 122.

It is to be understood that the above detailed description, including the various configurations of PTVI devices, is intended to be illustrative, and not restrictive. In general, cardiac protection pacing is applied to prevent or reduce cardiac injury and/or occurrences of arrhythmia caused by an ischemic event by using one or more pacing electrodes incorporated onto any intravascular device and a pacemaker that is capable of delivering pacing pulses according to a predetermined cardiac protection pacing sequence. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for placing a stent in a patient having a heart, the system comprising:
    a catheter including a proximal end portion, a distal end portion, and an elongate body extending therebetween, wherein the distal end portion includes an adjustable balloon for delivering the stent;
    one or more pacing electrodes configured to deliver pacing pulses to the heart; and
    a pacemaker configured to generate the pacing pulses to be delivered to the heart via the one or more pacing electrodes, wherein the pacing pulses are delivered at a rate substantially higher than the patient's intrinsic heart rate without being synchronized to the patient's intrinsic cardiac contractions and are delivered before, during, or after an ischemic event to prevent or reduce cardiac injury.

2. The system of claim 1 wherein the ischemic event is the occlusion of the blood vessel in which the stent is to be delivered.

3. The system of claim 1 wherein the pacemaker is an external pacemaker.

4. The system of claim 1, wherein the pacemaker is configured to cause the pacing pulses to be delivered at the rate substantially higher than the patient's intrinsic heart rate without being synchronized to the patient's intrinsic cardiac contractions during a pacing period programmable in a range of approximately 10 seconds to 20 minutes.

5. The system of claim 1, wherein a sequence of the pacing pulses are initiated during or after the ischemic event.

6. The system of claim 1, wherein a sequence of the pacing pulses are initiated after the ischemic event.

7. The system of claim 1, wherein the pacing pulses are delivered at the rate substantially higher than the patient's intrinsic heart rate during alternating pacing and non-pacing periods.

8. The system of claim 1, wherein the pacemaker is configured to cause the pacing pulses to be delivered at the rate substantially higher than the patient's intrinsic heart rate without being synchronized to the patient's intrinsic cardiac contractions during a pacing period programmable in a range of approximately 30 seconds to 20 minutes.

9. A method for delivering cardiac pacing to a patient, the method comprising:
    delivering a stent using a catheter including a stent delivery system causing an ischemic event in a patient; and
    pacing the heart of the patient before, during, or after the ischemic event in a manner such that pacing pulses are delivered at a rate substantially higher than the patient's intrinsic heart rate without being synchronized to the patient's intrinsic cardiac contractions.

10. The method of claim 9 wherein the pacing pulses are delivered before, during, or after an ischemic event to prevent or reduce cardiac injury.

11. The method of claim 9 wherein an external pacemaker is provided to pace the heart of the patient before, during, or after the ischemic event.

12. The method of claim 9 wherein the pacing pulses are delivered during a pacing period programmable in a range of approximately 10 seconds to 20 minutes.

13. The method of claim 9, wherein pacing the heart of the patient before, during, or after the ischemic event includes initiating a sequence of the pacing pulses during or after the ischemic event.

14. The method of claim 9, wherein pacing the heart includes delivering bipolar pacing of the heart using a bipolar configuration.

15. The method of claim 9, wherein pacing the heart includes delivering unipolar pacing of the heart using a unipolar configuration.

16. A system comprising:
    a stent;
    a catheter including a proximal end portion, a distal end portion, and an elongate body extending therebetween, wherein the distal end portion includes an adjustable balloon for delivering the stent;
    one or more pacing electrodes configured to deliver pacing pulses to a heart of a patient; and
    a pacemaker configured to generate the pacing pulses to be delivered to the heart via the one or more pacing electrodes, wherein the pacing pulses are delivered at a rate substantially higher than the patient's intrinsic heart rate without being synchronized to the patient's intrinsic cardiac contractions.

17. The system of claim 16, wherein the pacing pulses are delivered before, during, or after an ischemic event to prevent or reduce cardiac injury.

18. The system of claim 16 wherein the ischemic event is the occlusion of the blood vessel in which the stent is to be delivered.

19. The system of claim 16 wherein the pacemaker is an external pacemaker.

20. The system of claim 16 wherein the pacemaker is configured to cause the pacing pulses to be delivered at the rate substantially higher than the patient's intrinsic heart rate without being synchronized to the patient's intrinsic cardiac contractions during a pacing period programmable in a range of approximately 10 seconds to 20 minutes.

\* \* \* \* \*